US008634905B2

(12) United States Patent
Takiguchi

(10) Patent No.: US 8,634,905 B2
(45) Date of Patent: Jan. 21, 2014

(54) DETECTION APPARATUS AND DETECTION METHOD

(75) Inventor: Kiyoaki Takiguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 373 days.

(21) Appl. No.: 11/636,572

(22) Filed: Dec. 11, 2006

(65) Prior Publication Data

US 2007/0154878 A1 Jul. 5, 2007

(30) Foreign Application Priority Data

Dec. 12, 2005 (JP) ................. P2005-358306

(51) Int. Cl.
*A61B 5/053* (2006.01)

(52) U.S. Cl.
CPC .................. *A61B 5/0537* (2013.01)
USPC ........................................ 600/547

(58) Field of Classification Search
USPC .......................... 600/504, 506, 547
See application file for complete search history.

(56) References Cited

U.S. PATENT DOCUMENTS

| 5,526,808 | A | * | 6/1996 | Kaminsky ................ 600/370 |
| 5,787,185 | A |  | 7/1998 | Clayden |
| 6,577,897 | B1 | * | 6/2003 | Shurubura et al. ............ 600/547 |
| 7,225,009 | B2 | * | 5/2007 | Borgmeier et al. ........... 600/393 |
| 2004/0022421 | A1 | * | 2/2004 | Endoh et al. ................. 382/115 |
| 2004/0242989 | A1 | * | 12/2004 | Zhu et al. ..................... 600/407 |
| 2005/0148876 | A1 | * | 7/2005 | Endoh et al. .................. 600/454 |
| 2006/0085049 | A1 | * | 4/2006 | Cory et al. ....................... 607/48 |

FOREIGN PATENT DOCUMENTS

| JP | 11-203452 | 7/1999 |
| JP | 2005-073974 | 3/2005 |
| WO | WO 98/42255 | 10/1998 |
| WO | WO 2004/036379 | 4/2004 |
| WO | WO-2005020811 A * | 3/2005 ............... A61B 5/05 |

OTHER PUBLICATIONS

C. Gabriel, "Compilation of the dielectric properties of body tissues at RF and microwave frequences", Brooks Air Force Base, reports No. AL/OE-TR-1996-0037, 1996.

S. Gabriel et al., "The dielectric properties of biological tissues: III. Parametric models for the dielectric spectrum of tissues". Phys. Med. Biol. 41 (1996) 2271-2293.

Notification of Reasons for Refusal, issued by Japanese Patent Office on May 20, 2010 in the counterpart application No. 2005-358306.

* cited by examiner

*Primary Examiner* — Sean Dougherty
*Assistant Examiner* — Michael C Stout
(74) *Attorney, Agent, or Firm* — Finnegan, Henderson, Farabow, Garrett & Dunner, L.L.P.

(57) ABSTRACT

The present invention provides a detection apparatus, including: signal outputting means configured to output signals of a frequency band within which the difference in electric characteristic between different tissues of a living organism is higher than a predetermined level individually to two or more electrodes; impedance detection means configured to detect, from each of the electrodes, an impedance of the living organism disposed in quasi-electrostatic fields generated individually from the electrodes in response to the outputs; and colloid detection means configured to detect presence or absence of colloid in the inside of the living organism in response to the differences between the detected impedances.

6 Claims, 27 Drawing Sheets

FIG. 8

| Y \ X | -8mm | -4mm | 0mm | +4mm | +8mm |
|---|---|---|---|---|---|
| -8mm | 1847.962 | 1699.443 | 1045.017 | 1691.006 | 1913.218 |
| -4mm | 1891.955 | 1752.368 | 1020.877 | 1535.195 | 1655.657 |
| 0mm | 1869.896 | 1747.739 | 1059.97 | 1118.754 | 1107.589 |
| +4mm | 1937.46 | 1850.743 | 1713.557 | 1695.51 | 1632.057 |
| +8mm | 1913.665 | 1959.553 | 1913.7 | 1865.118 | 1939.946 |

FIG.13

| | IMPEDANCE R (ohm) |
|---|---:|
| FIG.11A | 1676 |
| FIG.11B | 1676 |
| FIG.12A | 1937 |
| FIG.12B | 1712 |

DETECTION APPARATUS AND DETECTION METHOD

CROSS REFERENCES TO RELATED APPLICATIONS

The present invention contains subject matter related to Japanese Patent Application JP 2005-358306 filed in the Japanese Patent Office on Dec. 12, 2005, the entire contents of which being incorporated herein by reference.

BACKGROUND OF THE INVENTION

1. Field of the Invention

This invention relates to a detection apparatus and a detection method and can be suitably applied typically in order to non-aggressively detect the state of a blood vessel.

2. Description of the Related Art

A measuring instrument which non-aggressively measures a living organism reaction in the inside of a living organism has been proposed by the assignee of the present application and is disclosed in Japanese Patent Laid-open No. 2005-73974.

According to the measuring instrument mentioned, a quasi-electrostatic field having intensity higher than that of an induction electromagnetic field at each of a plurality of distances individually corresponding to different frequencies is generated from a generation electrode. Then, the intensity variation of the quasi-electromagnetic field of the frequency corresponding to the distance is detected by a detection electrode. The measuring instrument detects, based on a result of the detection, living organism reactions which interact with the quasi-electromagnetic field such as, for example, two living organism reactions such as a double layer interface potential and a neural activity potential simultaneously.

SUMMARY OF THE INVENTION

However, in the measuring instrument having the configuration described above, although two different living organism reactions can be detected simultaneously, there is a problem that it cannot be specified by which tissues the living organism reactions are made.

Therefore, it is demanded to provide a detection apparatus and a detection method by which a particular detection object in a living organism can be detected with a high degree of accuracy.

According to an embodiment of the present invention, a detection apparatus includes signal outputting means configured to output signals of a frequency band within which the difference in electric characteristic between different tissues of a living organism is higher than a predetermined level individually to two or more electrodes, impedance detection means configured to detect, from each of the electrodes, an impedance of the living organism disposed in quasi-electrostatic fields generated individually from the electrodes in response to the outputs, and colloid detection means configured to detect presence or absence of colloid in the inside of the living organism in response to the differences between the detected impedances.

In the detection apparatus, an impedance of a quasi-electrostatic field of a frequency band in which the differences in electric characteristic among various living organism tissues are great is detected from each of the electrodes. Therefore, even if the electric characteristics of the tissues of the living organism are reflected on the impedances, whether or not the colloid exists in the quasi-electrostatic fields generated from the electrodes can be identified accurately from the differences between the impedances detected from the electrodes.

Further, in this instance, the frequency band in which the differences between the electric characteristics of the various tissues of the living organism are higher than the predetermined level is a low frequency region, and the quasi-electrostatic fields generated in response to the signals of the low frequency band prevail in intensity over the radiation fields and the induction electromagnetic fields. Therefore, the influence of the radiation fields and the induction electromagnetic fields is not reflected on the impedances detected by the individual electrodes through the quasi-electrostatic fields. Consequently, presence or absence of the colloid can be identified further accurately.

According to another embodiment of the present invention, a detection method includes a first step of outputting signals of a frequency band within which the difference in electric characteristic between different tissues of a living organism is higher than a predetermined level individually to two or more electrodes, a second step of detecting, from each of the electrodes, an impedance of the living organism disposed in quasi-electrostatic fields generated individually from the electrodes in response to the outputs, and a third step of detecting presence or absence of colloid in the inside of the living organism in response to the differences between the detected impedances.

In the detection method, an impedance of a quasi-electrostatic field of a frequency band in which the differences in electric characteristic among various living organism tissues are great is detected from each of the electrodes. Therefore, even if the electric characteristics of the tissues of the living organism are reflected on the impedances, whether or not the colloid exists in the quasi-electrostatic fields generated from the electrodes can be identified accurately from the differences between the impedances detected from the electrodes.

Further, in this instance, the frequency band in which the differences between the electric characteristics of the various tissues of the living organism are higher than the predetermined level is a low frequency region, and the quasi-electrostatic fields generated in response to the signals of the low frequency band prevail in intensity over the radiation fields and the induction electromagnetic fields. Therefore, the influence of the radiation fields and the induction electromagnetic fields is not reflected on the impedances detected by the individual electrodes through the quasi-electrostatic fields. Consequently, presence or absence of the colloid can be identified further accurately.

In summary, in the detection apparatus and the detection method, signals of a frequency band within which the difference in electric characteristic between different tissues of a living organism is higher than a predetermined level are outputted individually to two or more electrodes. Then, from each of the electrodes, an impedance of the living organism disposed in quasi-electrostatic fields generated individually from the electrodes in response to the outputs is detected. Thereafter, presence or absence of colloid in the inside of the living organism is detected in response to the differences between the detected impedances. Therefore, even if the electric characteristics of the tissues of the living organism are reflected on the impedances, whether or not the colloid exists in the quasi-electrostatic fields can be identified accurately from the differences between the impedances detected from the electrodes. Consequently, the particular detection object in the living organism can be detected with a high degree of accuracy.

BRIEF DESCRIPTION OF THE DRAWINGS

FIGS. 8 and 9 are a view and a diagram illustrating a simulation result by the second simulation model;

FIGS. 13 and 14 are views illustrating different simulation results by the third simulation model;

DETAILED DESCRIPTION OF THE PREFERRED EMBODIMENTS

1. Outline of the Embodiment

Figure 1:
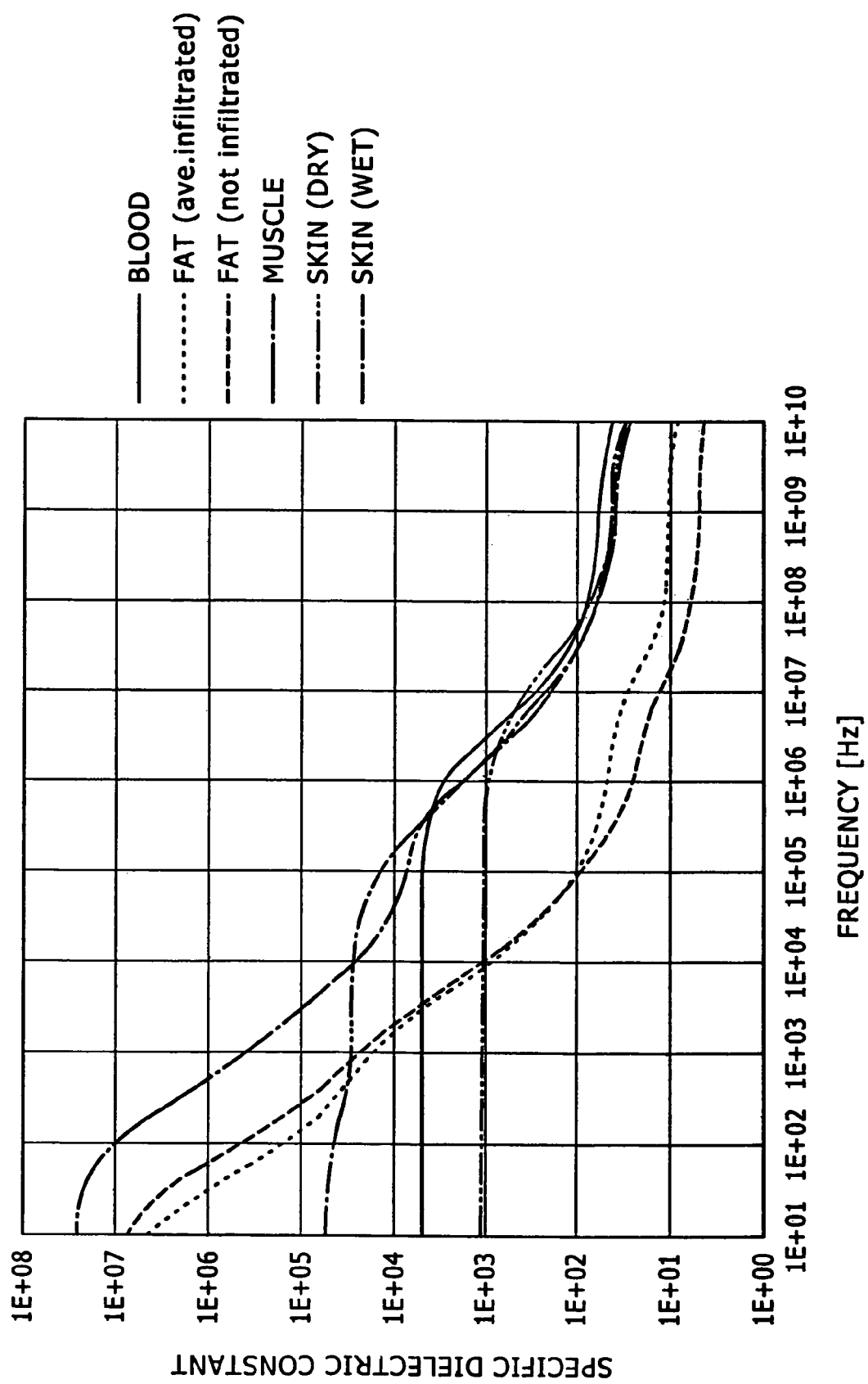
FIG. 1 is a diagram illustrating a relationship between the frequency and the conductivity at different tissues.
Figure 2:
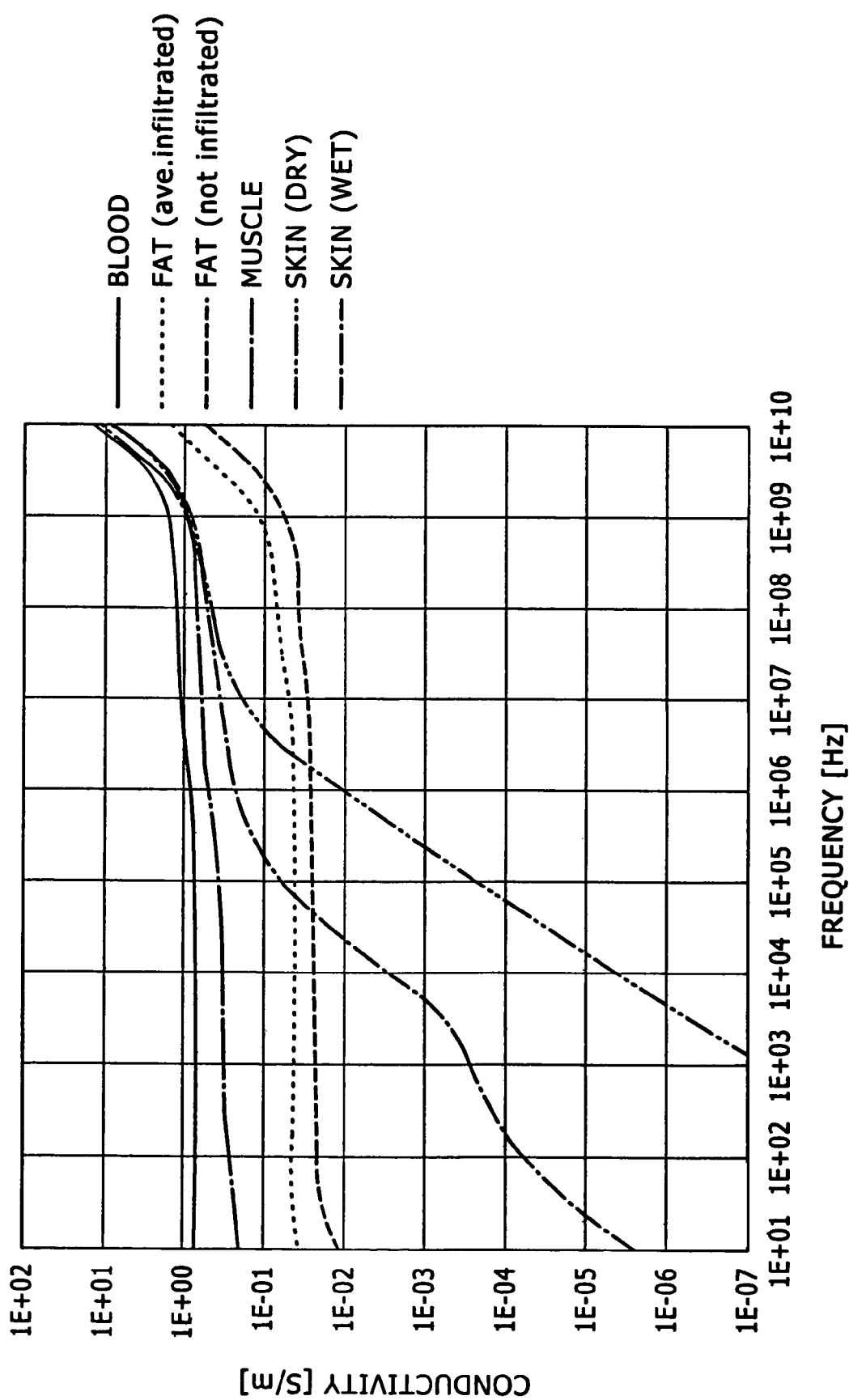
FIG. 2 is a diagram illustrating a relationship between the frequency and the specific dielectric constant at different tissues.

A relationship between the frequency and the specific dielectric constant at different internal tissues of the human body is illustrated in FIG. 1, and a relationship between the frequency and the conductivity is illustrated in FIG. 2. It is to be noted that, in FIGS. 1 and 2, the frequency, specific dielectric constant and conductivity are indicated in an exponential representation. Further, particular values of graphs of FIGS. 1 and 2 are based on Gabriel C. (1996), "Compilation of the dielectric properties of body tissues at RF and microwave frequencies", Books Air Force Base, reports No. Al/OE-TR-1996-0037 and so forth.

As can be recognized from FIGS. 1 and 2, the specific dielectric constant and the conductivity at each tissue is unique to the tissue. However, in a high frequency band, the specific dielectric constants and the conductivities at the different tissues exhibit comparatively small differences and are distributed thickly. Therefore, use of a high frequency band is disadvantageous to detection of a particular tissue.

In contrast, in a low frequency band, the specific dielectric constants and the conductivities at the different tissues exhibit comparatively great differences and are distributed discretely. Therefore, use of a low frequency band is advantageous to detection of a particular tissue. Particularly, at the blood, the specific dielectric constant and the conductivity are distinctly different from those at the other tissues over a frequency range from approximately 1 MHz to 10 MHz. Therefore, the blood is detected advantageously.

Taking notice of the fact that the electric characteristics (specific dielectric constant and conductivity) of the tissues in the low frequency band are distinctly different from each other, in the present embodiment, the state of the blood is detected non-aggressively from the epidermis based on a variation of the impedance of the living organism.

2. Simulation

Figure 3:
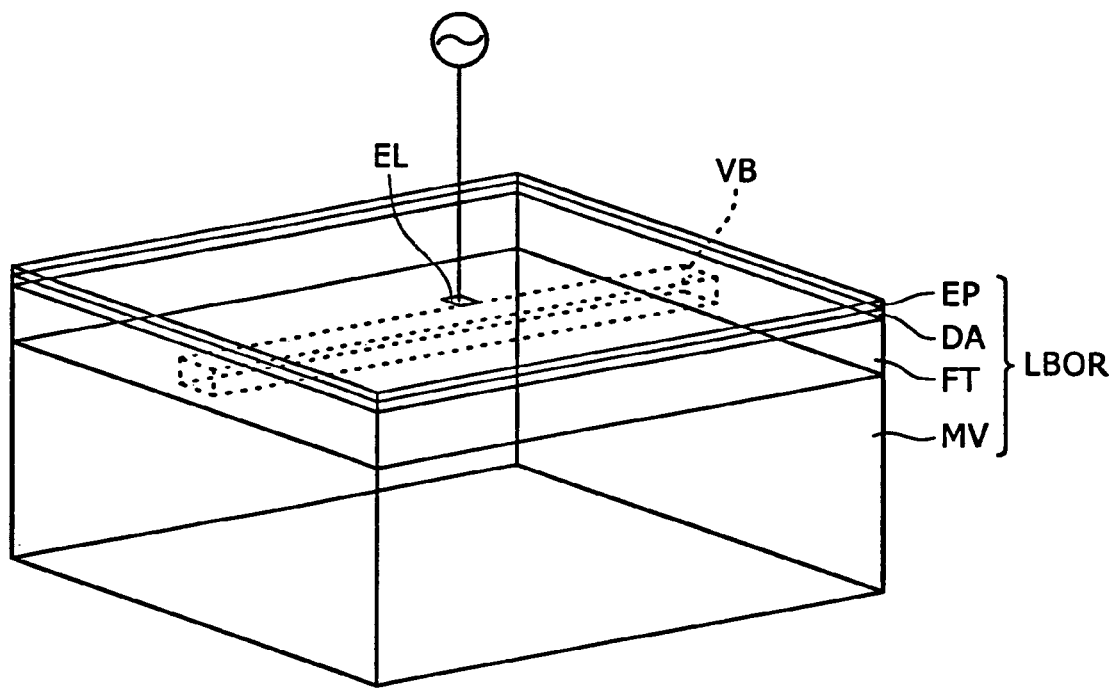
FIG. 3 is a schematic view showing a first simulation model.

A simulation was conducted with regard to the detection method. The simulation model (hereinafter referred to as first simulation model) is carried out in such a manner as seen in FIG. 3. Referring to FIG. 3, one electrode EL is disposed on the surface of living organism tissues LBOR including an epidermis layer EP of 0.5 mm thick, a dermis layer DA of 0.5 mm thick, a fat layer FT of 4 mm thick and a muscle layer MV of 15 mm thick. Then, various signals having a fixed amplitude but having frequencies from 1 to 100 MHz are applied individually to the electrode EL.

Figure 4:
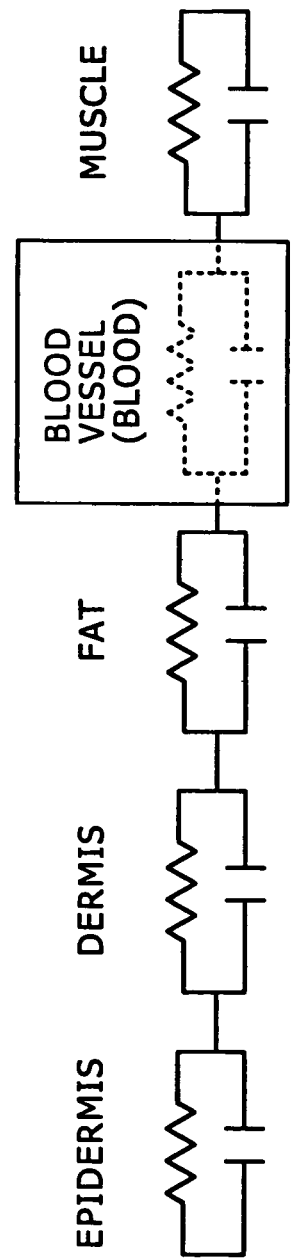
FIG. 4 is a circuit diagram showing an equivalent circuit to living organism tissues.

At this time, a case that a blood vessel VB exists in the fat layer FT and another case that no blood vessel VB exists in the fat layer FT were supposed, and the impedance of the living organism tissues LBOR obtained from the electrode Et in these instances was measured. The equivalent circuit of the living organism tissues LBOR in this instance is such as shown in FIG. 4. It is to be noted that the electric characteristic of the blood vessel VB is set equal to that of the blood.

Figure 5:
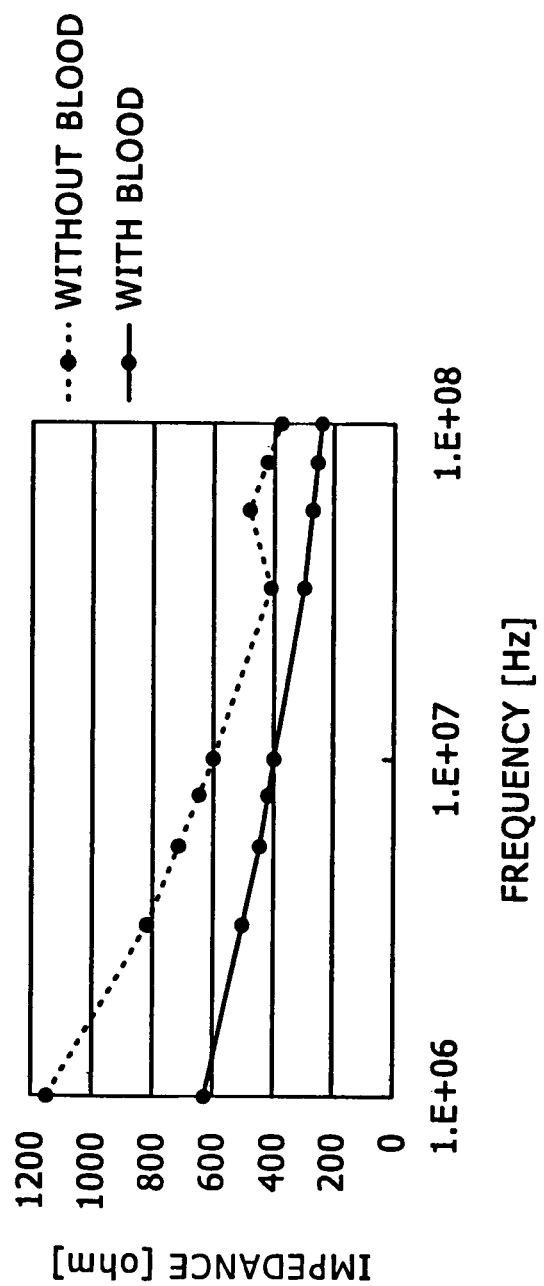
FIG. 5 is a diagram illustrating a simulation result by the first simulation model.

A result of the simulation with the first simulation model is illustrated in FIG. 5. It is to be noted that the frequency in FIG. 5 is indicated in an exponential representation while the impedance is indicated in a real part component. As can be seen apparently from FIG. 5, the presence or absence of the blood vessel VB is reflected on an integrated result of the impedance at the epidermis, dermis, fat, blood and muscle. It can be seen that the presence or absence of the blood vessel VB is reflected more clearly particularly in a low frequency band.

Figure 6:
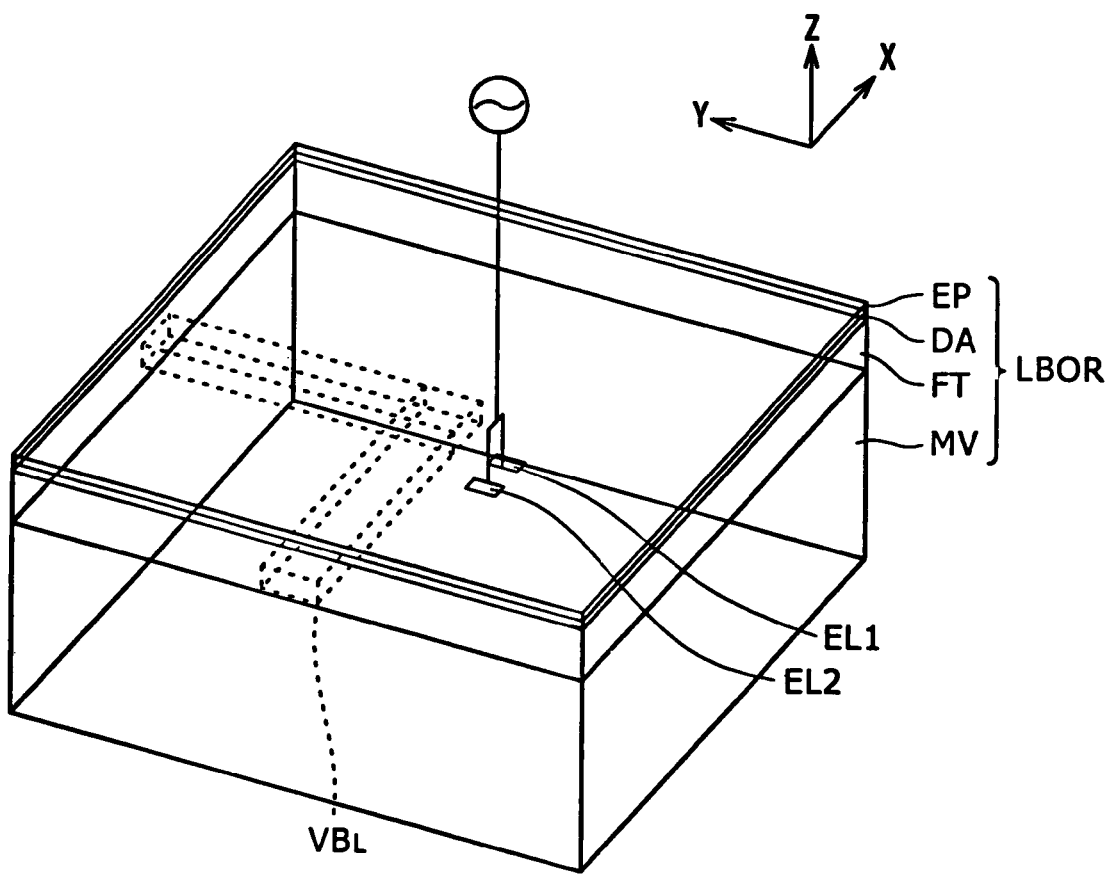
FIG. 6 is a schematic view showing a second simulation model.

FIG. 6 illustrates another simulation model (hereinafter referred to as second simulation model). Referring to FIG. 6, according to the second simulation model, a signal having a fixed amplitude and a fixed frequency of 1 MHz is applied to two electrodes EL1 and EL2 disposed on the surface of living organism tissues LBOR which includes an L-shaped blood vessel $VB_L$ in a fat layer FT thereof.

At this time, the disposed positions of the electrodes EL1 and EL2 were successively set to the bent position of the L-shaped blood vessel $VB_L$ and a plurality of positions around the bent position, and the impedance of the living organism tissues LBOR detected from the electrodes EL1 and EL2 disposed at the positions was measured.

Figure 7:
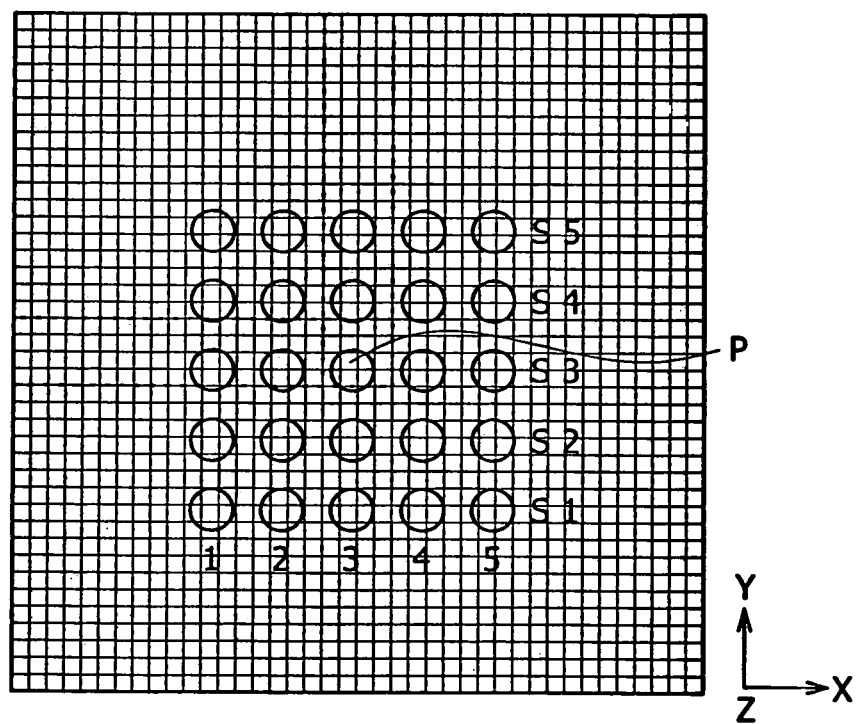
FIG. 7 is a schematic view showing arrangement of electrodes.

The disposed positions of the electrodes EL1 and EL2 were 25 positions defined by five positions at −8 mm, −4 mm, 0 mm, 4 mm and 8 mm in an x direction and five positions at −8 mm, −4 mm, 0 mm, 4 mm and 8 mm in a y direction where the bent position P of the L-shaped blood vessel VBL is defined as the origin as seen in FIG. 7.

Figure 9:
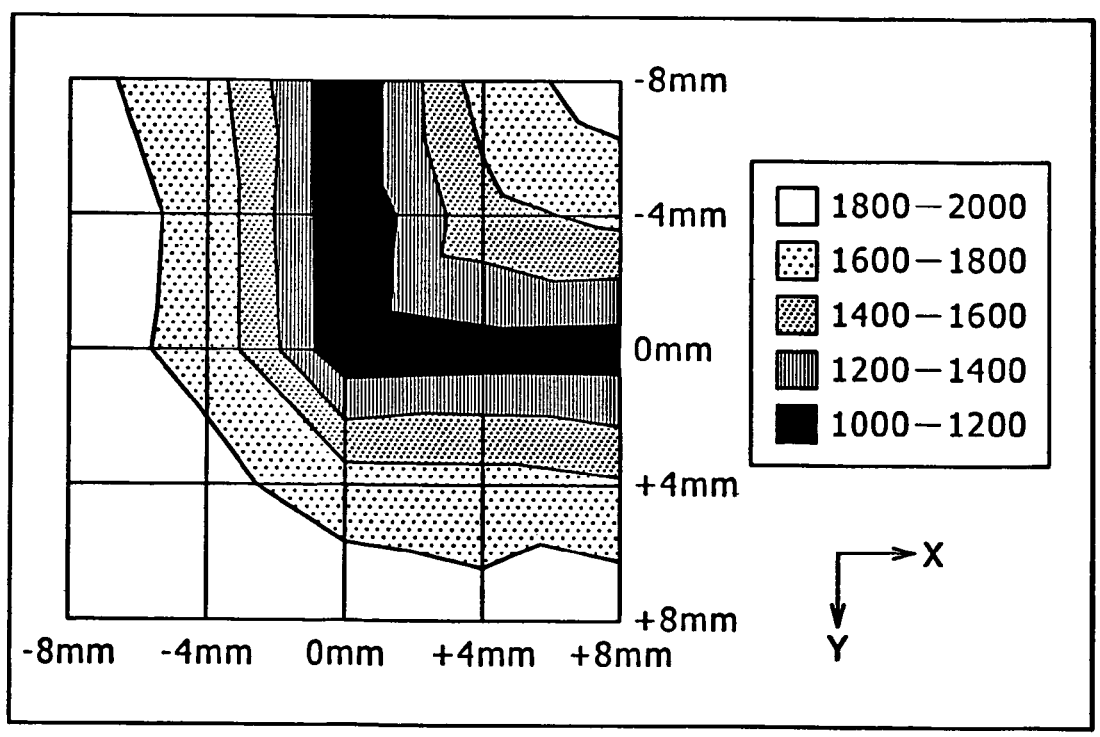

A result of the simulation with the second simulation model is illustrated in FIGS. 8 and 9. Incidentally, the impedance in FIG. 8 is indicated only in a real part component. Meanwhile, FIG. 9 visually illustrates the impedance values of FIG. 8, and impedance values at the other positions than the disposed positions of the electrodes EL1 and EL2 were obtained by interpolation.

As can be seen apparently from FIGS. 8 and 9, as the electrode disposed position approaches the vessel (blood), the impedance decreases. From this, it can be recognized that it is possible to decide that a blood vessel exists under an electrode which exhibits a low impedance.

Figure 10:
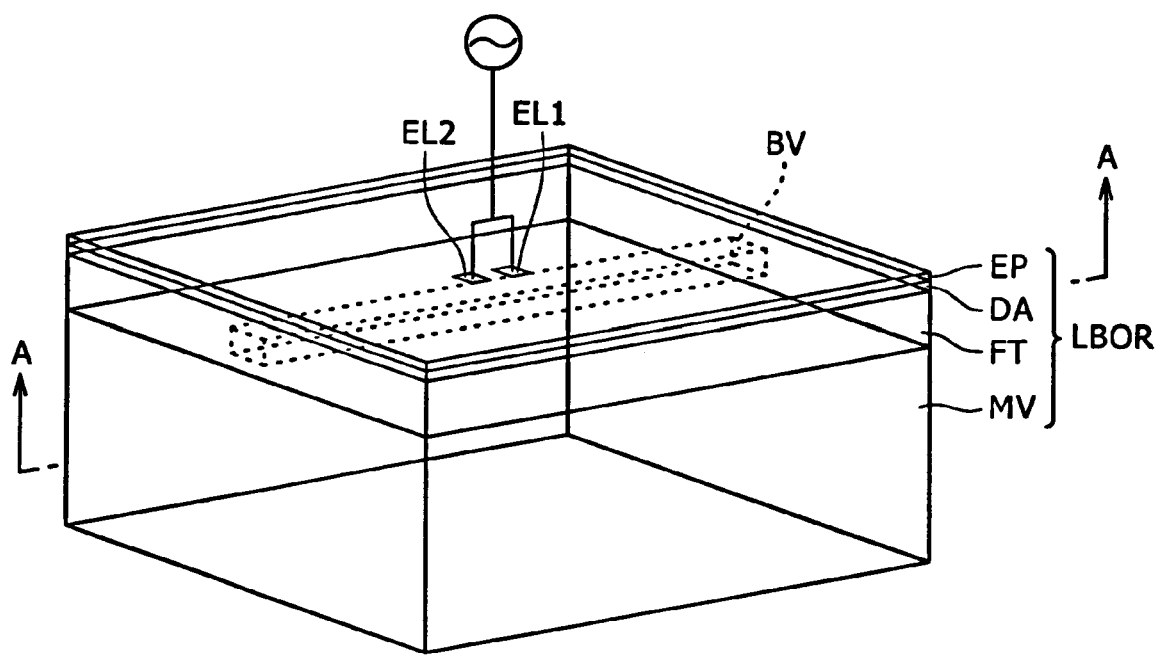
FIG. 10 is a schematic view showing a third simulation model.

Meanwhile, FIG. 10 illustrates a further simulation model. (hereinafter referred to as third simulation model). Referring to FIG. 10, in the third simulation model, a signal having a fixed amplitude and a fixed frequency of 1 MHz is applied to two electrodes EL1 and EL2 disposed on the surface of living organism tissues LBOR.

Figure 11A:
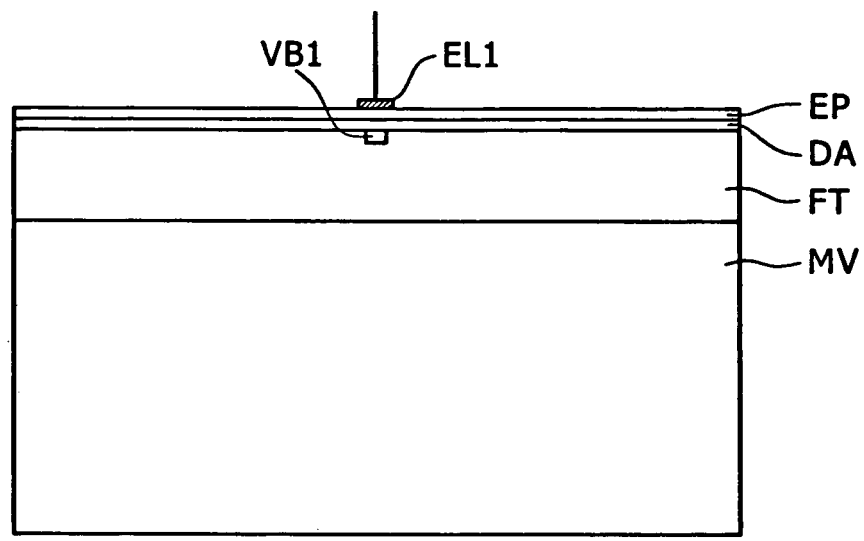
FIGS. 11A, 11B, 12A and 12B are schematic views illustrating measurement with different electrodes for different blood vessel diameters and depths.

At this time, as seen from FIG. 11 which is a sectional view taken along line A-A' of FIG. 10, the impedance of the living organism tissues LBOR detected from the electrode EL1 was measured in a case that a blood vessel VB1 of a cross section of 1 mm×0.5 mm exists at the position of 1 mm from the surface (FIG. 11A) and another case that a blood vessel VB2 of a cross section of 4 mm×3.5 mm exists at the position of 1.5 mm from the surface.

Figure 11B:
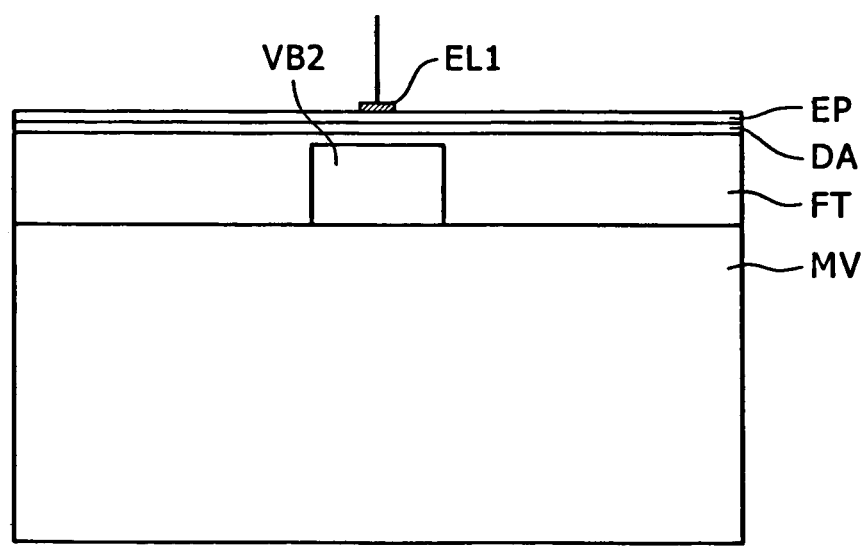
Figure 12A:
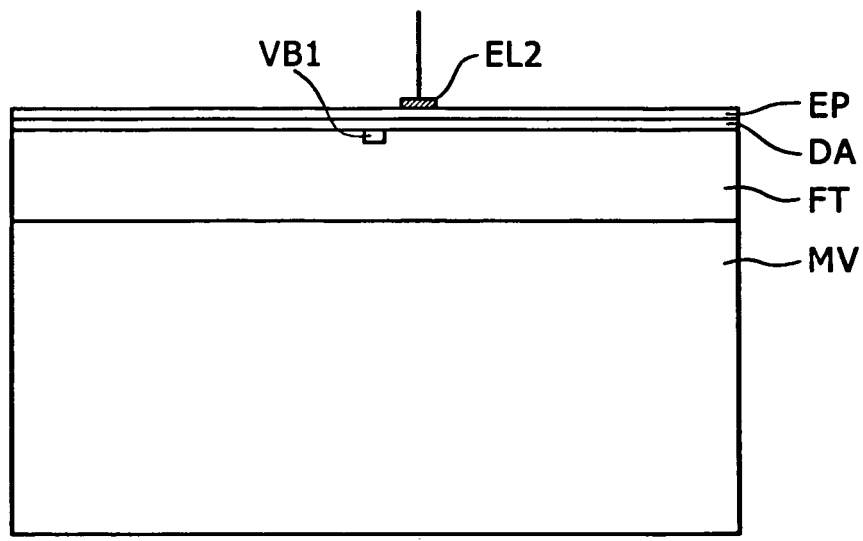
Figure 12B:
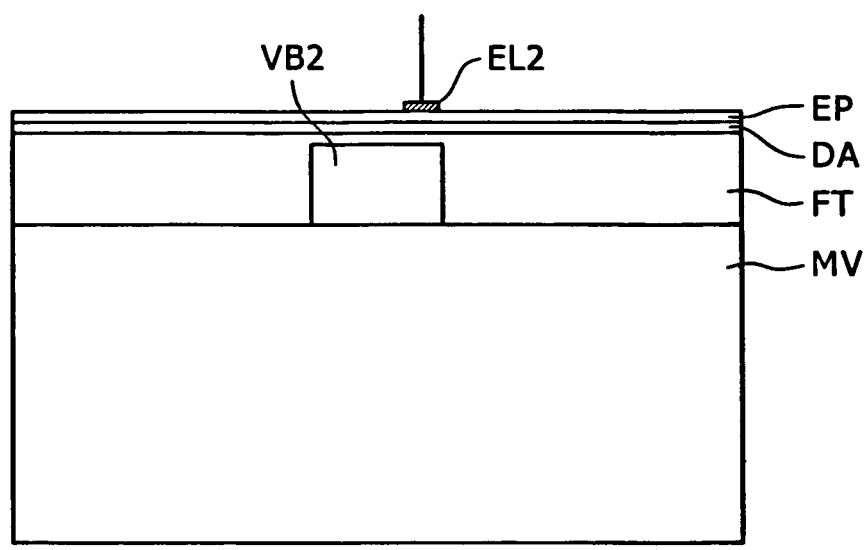

Further, the impedance of the living organism tissues LBOR detected from the other electrode EL2 displaced by 2 mm from the position of the electrode EL1 in the case of FIG. 11A as seen in FIG. 12A and the impedance of the living organism tissues LBOR detected from the electrode EL2 displaced by 2 mm from the position of the electrode EL1 in the case of FIG. 11B as seen in FIG. 12B were measured.

A result of the simulation with the third simulation model is illustrated in FIG. 13. It is to be noted that the impedance in FIG. 13 is indicated only in a real part component. As can be seen apparently also from FIG. 13, since the distance between the electrode EL1 and the blood is small, a result of measurement of the impedance is not reflected on the electrode EL1, but since the distance between the electrode EL2 and the blood is great to some degree, a result of measurement of the impedance is reflected on the electrode EL2.

In particular, where the blood vessel is thick, since the distance between the electrode EL2 and the blood is smaller than that where the blood vessel is thin, the impedance is high. Also where the distance from the surface of the living organism to the blood vessel (the distance is hereinafter referred to as blood vessel depth) is great, since the distance between the electrode EL2 and the blood is smaller that that where the blood vessel depth is small, the impedance is high. The facts described can be recognized also from the simulation result of FIG. 13.

From this, if attention is paid to only one of the electrodes, then the difference in thickness of the blood vessel and in blood vessel depth cannot be decided from a result of measurement of the impedance, but if attention is paid to both of the two electrodes, then the thickness of the blood vessel and the blood vessel depth can be decided from the distance between the electrodes and the impedances detected from the electrodes. Further, if the number of electrodes is increased, then the accuracy in detection can be enhanced.

On the other hand, in the first simulation model (FIG. 3), the signal to be applied to the electrode EL is changed to a signal having a fixed amplitude and a fixed frequency of 1 MHz. Then, supposing that the specific dielectric constant of the blood in the blood vessel VB which exists in the fat layer FT of the living organism tissues LBOR successively assumes values of "1,000", "2,000", "3,000", "4,000" and "5,000", the impedance of the living organism tissues LBOR detected from the electrode EL was measured in those cases.

Figure 14:
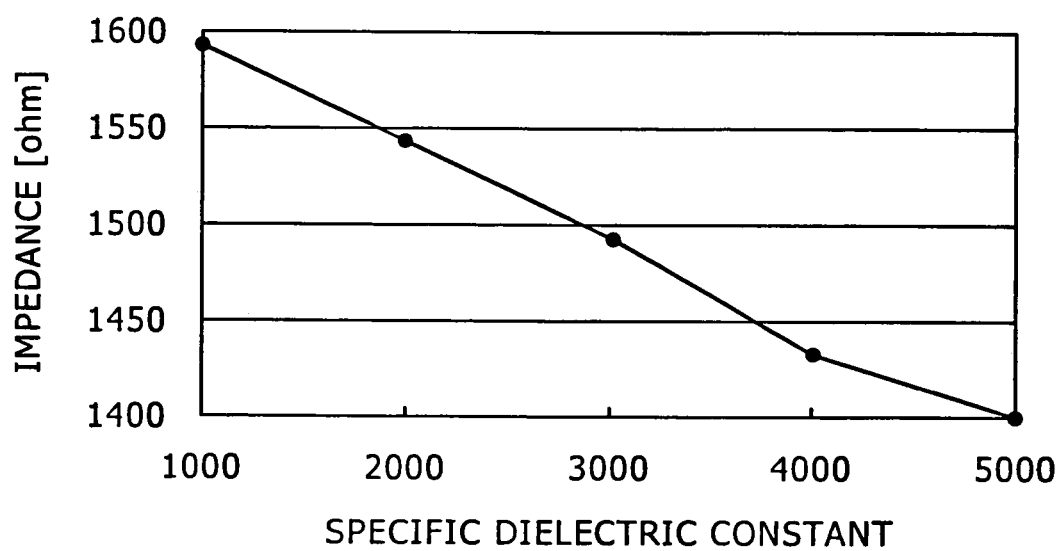

A result of the simulation in this instance is illustrated in FIG. 14. It is to be noted that the impedance in FIG. 14 is indicated only in a real part component. As can be seen also from FIG. 14, the integrated result of the impedances at the epidermis, dermis, fat, blood and muscle and the specific dielectric constant have a correlation to each other.

If water particles of W/O (Water in Oil emulsion) cohere, then the dielectric constant increases. This is because it is considered that a structure which electrically interconnects water particles is formed on the oil-phase face on the outer side of the water particles. This similarly applies also to the blood, and if roleaux or aggregates of red blood corpuscles are produced, then the dielectric constant increases. This is disclosed, for example, also in Tetsuya HANAI, "Heterogeneity and Dielectric Constant", Yoshioka Shoten. From this, the state of red blood corpuscles (roleaux, aggregates or the like), that is, the blood vessel viscosity, can be decided in response to the impedance values.

As can be recognized also from the simulations described above, the presence or absence of the blood, the blood vessel diameter, the blood vessel depth and the state of the blood can be detected non-aggressively from the epidermis based on a variation of the impedance of the blood.

It is to be noted that, in the simulations described above, the electromagnetic wave general purpose analysis software "EEM-FDM" by Information and Mathematical Science Laboratory Inc. was adopted as the calculation method of the impedance. This software discretizes a Maxwell equation regarding a designated frequency using a finite difference method and calculates the impedance of an electric field or a magnetic field in the space or between feed electrodes.

3. Relationship between the Frequency and the Electric Field

It is apparent from the simulation results described hereinabove that the conductivities and the specific dielectric constants at individual tissues exhibit great differences and are discretized in a low frequency band. A particular tissue can be detected advantageously. In the following, a relationship between the frequency and the electric field is described.

Where the distance from a very small dipole which serves as an electric field generation source is represented by r and the position spaced by the distance r is represented by P, the electric field intensity E at the position P can be represented as polar coordinates (r, θ, δ) from a Maxwell equation like the following expressions:

$$E_r = \frac{Q1\cos\theta}{2\pi\varepsilon r^3}(1 + jkr)\exp(-jkr) \quad (1)$$

$$E_\theta = \frac{Q1\sin\theta}{4\pi\varepsilon r^3}(1 + jkr + (jkr)^2)\exp(-jkr)$$

where Q is the charge C, l the distance between charges (where, from the definition of a very small dipole, l is smaller than r), π the number π, ∈ the dielectric constant of the space including the very small dipole, j the imaginary unit, and k the wave number.

By developing the expressions (1), the following expressions (2) are obtained:

$$E_r = \frac{Q1\cos\theta}{2\pi\varepsilon r^3} \cdot \exp(-jkr) + \frac{Q1\cos\theta}{2\pi\varepsilon r^3} \cdot jkr \cdot \exp(-jkr) \quad (2)$$

$$E_\theta = \frac{Q1\sin\theta}{4\pi\varepsilon r^3} \cdot \exp(-jkr) +$$
$$\frac{Q1\sin\theta}{4\pi\varepsilon r^3} \cdot jkr \cdot \exp(-jkr) + \frac{Q1\sin\theta}{4\pi\varepsilon r^3} \cdot (jkr)^2 \cdot \exp(-jkr)$$

As can be recognized from the expressions (2), the electric fields $E_r$ and $E_\theta$ are generated as a composite electric field of a radiation field (third term of $E_\theta$) which increases linearly in inverse proportion to the distance from the electric field generation source, an induction electromagnetic field (second term of $E_r$ and $E_\theta$) which increases in inverse proportion to the square of the distance from the electric field generation source and a quasi-electrostatic field (first term of $E_r$ and $E_\theta$) which increases in proportion to the cube of the distance from the electric field generation source.

Here, the ratio at which the electric field intensity varies in response to the distance from the electric field generation source is compared between a radiation field, an induction electromagnetic field and a quasi-electrostatic field. By differentiating the third term relating to the radiation field from within the electric field Ee in the expression (2) with the distance r, the following expression (3) is obtained:

$$\frac{dE_{\theta 1}}{dr} = -\frac{1}{r^2}T \quad (3)$$

Further, by differentiating the second term relating to the induction electric field from within the electric field $E_\theta$ in the expression (2) with the distance r, the following expression (4) is obtained:

$$\frac{dE_{\theta 2}}{dr} = -2\frac{1}{r^3}T \quad (4)$$

Furthermore, by differentiating the first term relating to the quasi-electrostatic field from within the electric field $E_\theta$ in the expression (2) with the distance r, the following expression (4) is obtained:

$$\frac{dE_{\theta 3}}{dr} = -3\frac{1}{r^4}T \quad (5)$$

In the expressions (3) to (5), T is used for simplification and represents $$T = \frac{Q1\cos\theta}{2\pi\varepsilon r^3} \cdot \exp(-jkr) \quad (6)$$

which is part of the expression (2) above.

As can be recognized from the expressions (3) to (5), the rate at which the electric field intensity varies in response to the distance is highest at the component relating to the quasi-electrostatic field. In other words, the quasi-electrostatic field has a high resolution to the distance. Accordingly, if the intensity of the induction electromagnetic field and the radiation field from within the electric field generated from the electric field generation source decreases, then the impedance of a living organism tissue can be measured with a high degree of accuracy.

Figure 15:
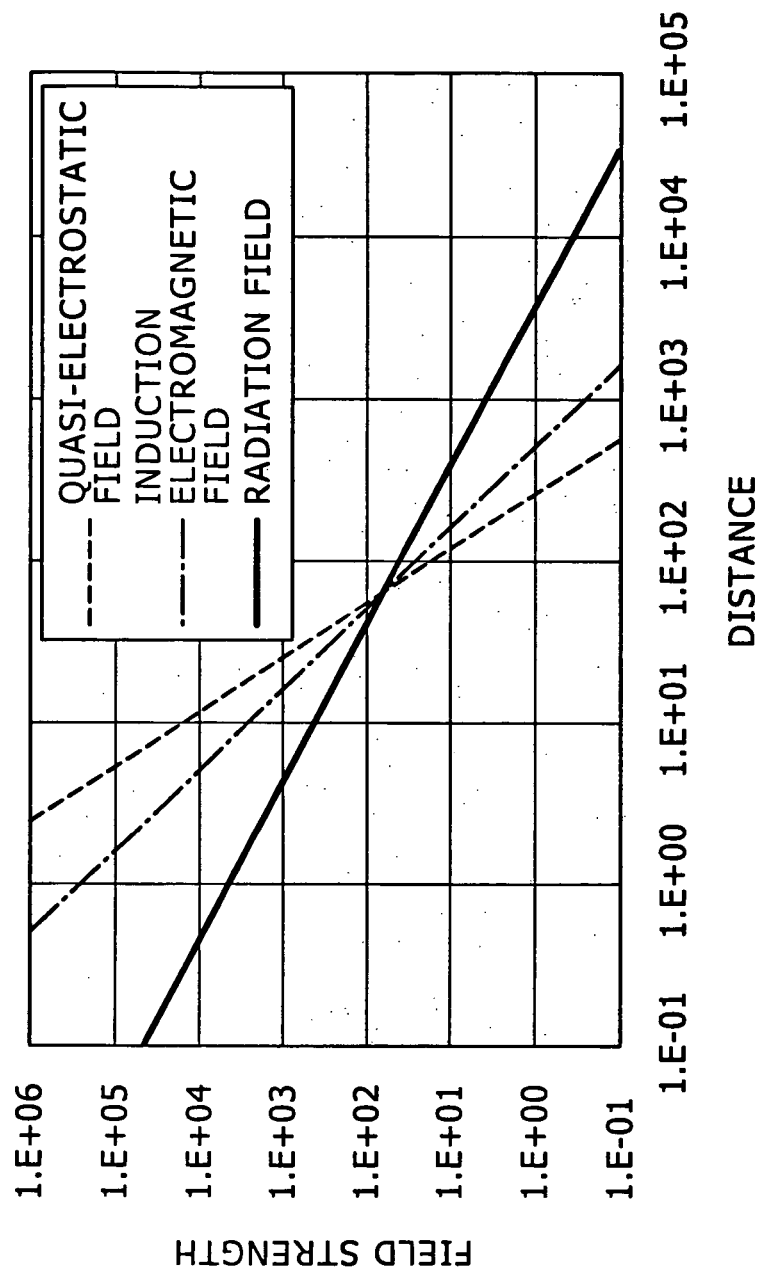
FIGS. 15 and 16 are diagrams illustrating different relative intensity variations of different electric fields with respect to the distance.

Here, the relationships between relative intensities of the radiation field, induction electromagnetic field and quasi-electrostatic field and the distance can be represented as such graphs as shown in FIG. 15. It is to be noted that, FIG. 15, the relationship between the relative intensity of each of the electric fields of 1 MHz and the distance is indicated in a real part component.

As can be recognized from FIG. 15, there exists a distance at which the relative intensities of the radiation field, induction electromagnetic field and quasi-electrostatic field are equal to each other. The distance is hereinafter referred to as intensity boundary point. In this instance, in a space farther than the intensity boundary point, the radiation field prevails over the induction field and the quasi-electrostatic field. On the contrary, in another space nearer than the intensity boundary point, the quasi-electrostatic field prevails over the radiation field and the induction electromagnetic field.

At the intensity boundary point, the components of the electric field corresponding to the terms ($E_{\theta 1}$, $E_{\theta 2}$, $E_{\theta 3}$) of the electric field $E_\theta$ in the expression (2), that is, the values given by the following expressions (7):

$$E_{\theta 1} = \frac{Q1\sin\theta}{4\pi\varepsilon r^3} \cdot \exp(-jkr) \quad (7)$$

$$E_{\theta 2} = \frac{Q1\sin\theta}{4\pi\varepsilon r^3} \cdot jkr \cdot \exp(-jkr)$$

$$E_{\theta 3} = \frac{Q1\sin\theta}{4\pi\varepsilon r^3} \cdot (jkr)^2 \cdot \exp(-jkr)$$

coincide with each other ($E_{\theta 1}=E_{\theta 2}=E_{\theta 3}$). Therefore, the intensity boundary point satisfies the following expression (8):

$$1=jkr=(jkr)^2 \quad (8)$$

and hence can be represented by the following expression (9):

$$r = \frac{1}{k} \quad (9)$$

Then, the wave number k in the expression (9) above can be represented, where the propagation velocity of the electric field through the medium is v m/s and the frequency is f Hz, by the following expression (10):

$$k = \frac{2\pi f}{v} \quad (10)$$

Further, the propagation velocity v of the electric field is represented, where the velocity of light is c m/s ($c=3\times10^8$, from the velocity c of light and the specific dielectric constant ∈ of the dielectric constant medium in the space including the very small dipole by the following expression (11):

$$v = \frac{c}{\sqrt{\varepsilon}} \quad (11)$$

Therefore, the intensity boundary point can be represented, by substituting the expressions (10) and (11) into the expression (9), by the following expression (12):

$$r = \frac{C}{2\pi f \cdot \sqrt{\varepsilon}} \quad (12)$$

As can be recognized from the expression (12), where it is intended to widen the space of the quasi-electrostatic field which has a higher intensity than the radiation field and the induction electromagnetic field (the space is hereinafter referred to as quasi-electromagnetic field prevailing space), the frequency relates closely to this. In particular, as the frequency decreases, the quasi-electrostatic field prevailing space increases. In other words, the distance to the intensity boundary point shown in FIG. 15 increases as the frequency decreases, that is, the intensity boundary point moves to the right as the frequency decreases. On the other hand, as the frequency increases, the quasi-electrostatic field prevailing space decreases. In other words, the distance to the intensity boundary point shown in FIG. 15 decreases as the frequency increases, that is, the intensity boundary point moves to the left as the frequency decreases.

For example, if the frequency is set to 10 MHz, then if it is assumed that the specific dielectric constant of the human body is uniformly 50, then a space in which the quasi-electrostatic field prevails is formed on the shorter side of the frequency than 0.675 m from the expression (12) given hereinabove. Where the frequency is set to 10 MHz in this manner, the relationships between the relative intensities of the radiation field, induction electromagnetic field and quasi-electric field and the distance can be represented as such graphs as shown in FIG. 16.

Figure 16:
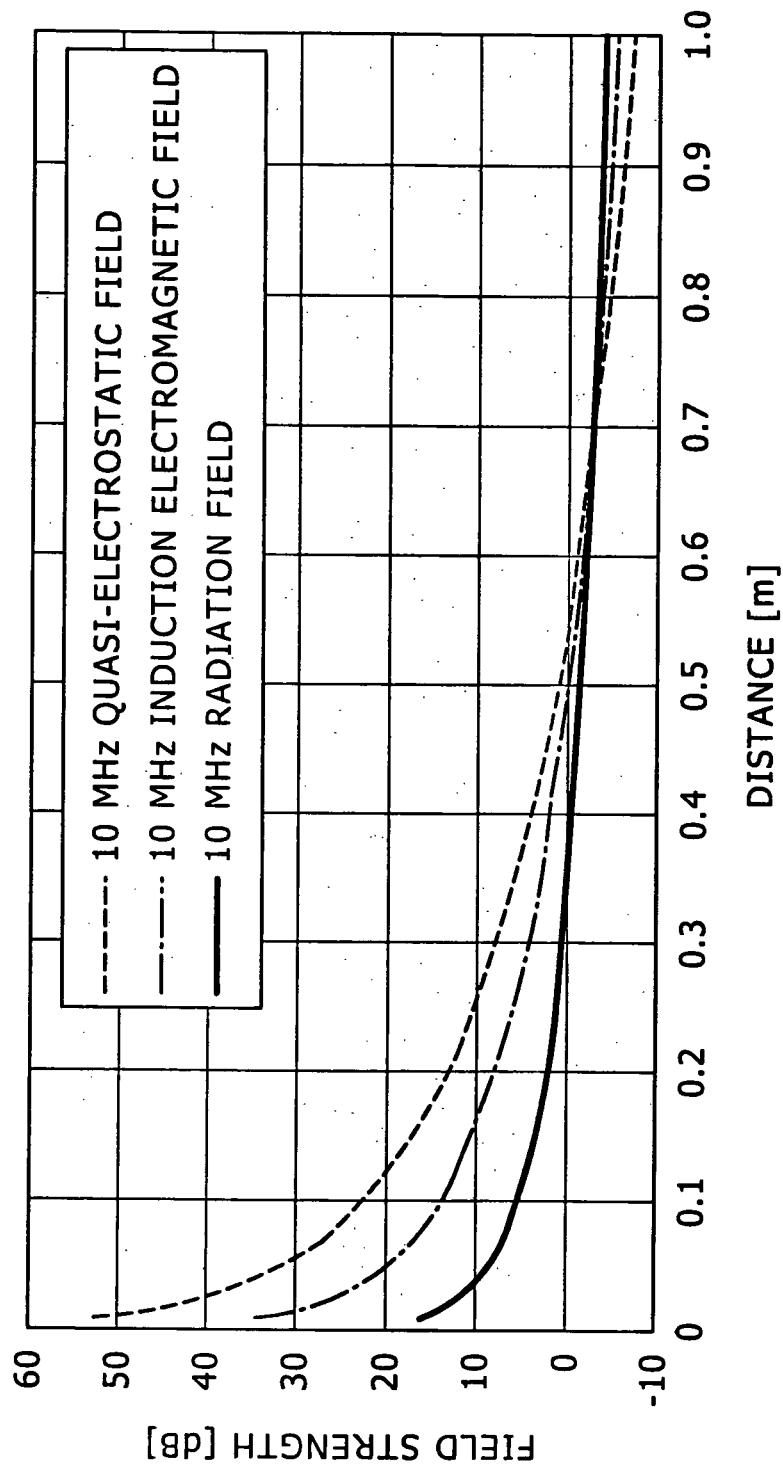

As can be recognized from FIG. 16, the intensity of the quasi-electrostatic field at a point of 0.01 m from the electric field generation source is higher by approximately 18.2 dB than that of the induction electromagnetic field. Accordingly, it can be considered that the quasi-electrostatic field in this instance is free from an influence of the induction electric field and the radiation field.

It can be recognized that, if a low frequency band is selected in this manner, then since the intensities of the induction electromagnetic field and the radiation field from within the electric field generated from the electric field generation source relatively decrease, the impedance of an organism tissue can be detected with a high degree of accuracy.

As described above, a low frequency band is used advantageously to detect a particular tissue not only from a point of view of the conductivity and the specific dielectric constant of tissues but also from a point of view of the influence of the induction electromagnetic field and the radiation field.

4. First Embodiment

4-1. Configuration of the Detection Apparatus

Figure 17:
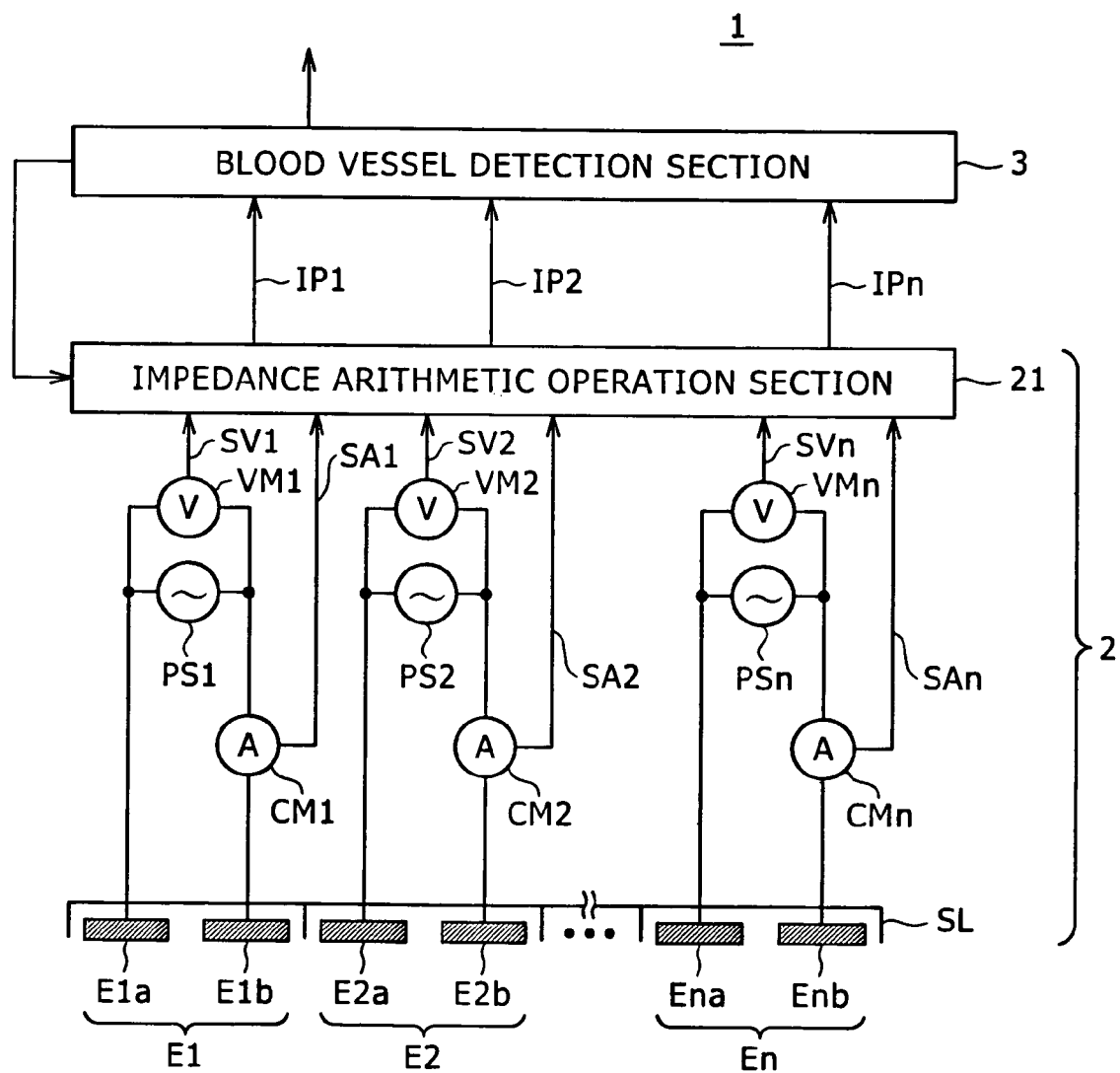
FIG. 17 is a block diagram showing a configuration of a detection apparatus to which the present invention is applied.

A detection apparatus for detecting a particular tissue from the impedance of the organization of a living organism as an embodiment of the present invention is shown in FIG. 17. Referring to FIG. 17, the detection apparatus 1 shown includes an impedance detection section 2 and a blood vessel detection section 3.

4-2. Configuration of the Impedance Detection Section

The impedance detection section 2 includes a plurality of electrodes E1 (E1a, E1b), E2 (E2a, E2b), . . . , En (Ena, Enb) disposed in a grating fashion and forming a plurality of sets each of which includes a reference electrode and another electrode paired with the reference electrode. For example, signals having a fixed amplitude and a frequency of 1 MHz are outputted from signal supplying sources PS1 to PSn to the electrodes E1 to En, respectively.

Incidentally, in FIG. 17, the electrodes E1 to En are shown in a form arrayed on a line for the convenience of illustration. Further, the signals to be outputted to the electrodes E1 to En are selected using the frequency below which the conductivity and the specific dielectric constant of a living organism tissue to be determined as a detection object can be distinguished clearly from those of the other tissues and the depth of the living organism tissue to be determined as a detection object from the surface of the living organism, and so forth as indicators or indices.

Where such signals as described above are applied to the electrodes E1 to En, the electrodes E1 to En oscillate in response to the signals and generate quasi-electrostatic fields. The quasi-electrostatic fields prevail in the space nearer to the electrodes, that is, the intensity of the quasi-electrostatic fields is higher than those of the radiation fields and the induction electromagnetic fields. In the tissues of the living organism, potentials are generated in response to the quasi-electrostatic fields.

In this instance, measurement results SA1 to SAn by ammeters CM1 to CMn provided for the electrodes E1 to En, respectively, and measurement results. SV1 to SVn by voltmeters VM1 to VMn provided for the signal supplying sources PS1 to PSn, respectively, are inputted to an impedance arithmetic operation section 21 of the impedance detection section 2.

The impedance arithmetic operation section 21 determines the ratio between the measurement result SA1 of the ammeter CM1 and the measurement result SV1 of the voltmeter VM1, the ratio between the measurement result SA2 of the ammeter CM2 and the measurement result SV2 of the voltmeter VM2, . . . , and the measurement result SAn of the ammeter CMn and the measurement result SVn of the voltmeter VMn. Then, the impedance arithmetic operation section 21 determines the impedance values of the electrodes E1 to En from the thus determined ratios. Incidentally, while each of the impedance values is obtained as a complex number, it is preferable to adopt that one of a real part component, an imaginary part component and a combination of the components which has the highest sensitivity.

Then the impedance arithmetic operation section 21 outputs the impedance values corresponding to the electrodes E1 to En as data (hereinafter referred to as impedance data) IP1 to IPn to the blood vessel detection section 3.

In this manner, the impedance detection section 2 can detect the impedance of a living organism tissue.

Figure 18:
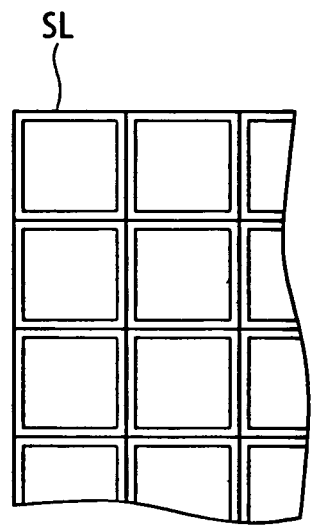
FIG. 18 is a schematic view showing a configuration of a shield used in the detection apparatus of FIG. 17.

In addition, a conductive shield SL is provided for the impedance detection section 2 in an electrically isolated state from the electrodes E1 to En as seen in FIGS. 17 and 18. The shield SL partitions the electrodes E1 to En from each other with partition walls thereof.

Accordingly, in the impedance detection section 2, the electrodes E1 to En are covered with the partition walls of the shield SL except the direction in which the electric fields are to be irradiated. Therefore, the directivity of the quasi-electrostatic fields to be emitted from the electrodes E1 to En can be enhanced, and besides such a situation that external noise different from the quasi-electrostatic fields comes round to the electrodes E1 to En can be prevented. As a result, the accuracy in detection of the impedance of a tissue of a living organism can be enhanced.

Further, the shield SL is formed from a material having flexibility. Consequently, with the impedance detection section 2, the electrodes E1 to En can be contacted closely with a living organism. Consequently, the accuracy in detection of the impedance of a living organism tissue can be further enhanced.

4-3. Configuration of the Blood Vessel Detection Section.

Figure 19:
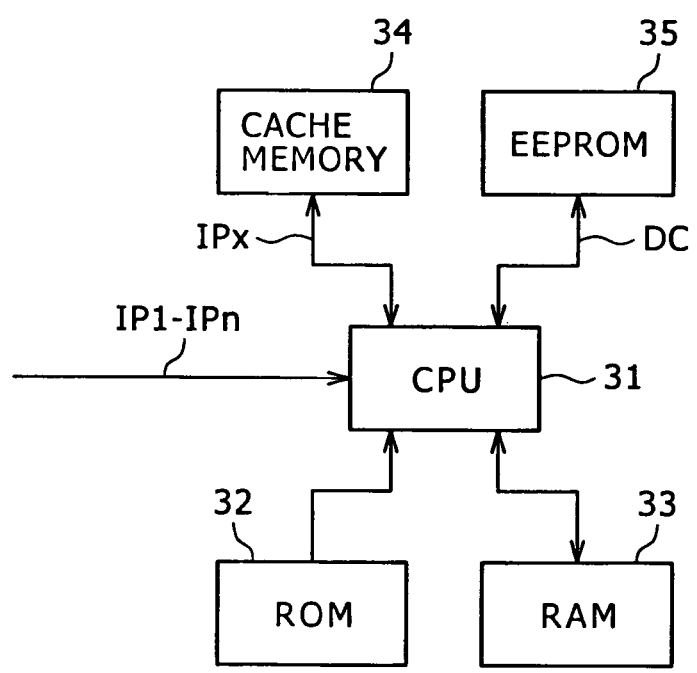
FIG. 19 is a block diagram showing a configuration of a blood vessel detection section of the detection apparatus of FIG. 17.

Meanwhile, referring to FIG. 19, the blood vessel detection section 3 includes a ROM (Read Only Memory) 32 for storing a predetermined program, a RAM (Random Access Memory) 33 serving as a working memory, a cache memory 34 and an EEPROM (Electrically Erasable Programmable ROM) 35 all connected to a CPU (central processing unit) 31.

The CPU 31 suitably controls the cache memory 34, EEPROM 35 and impedance arithmetic operation section 21 (FIG. 17) in accordance with the program stored in the ROM 32 to execute a blood vessel detection process.

Figure 20:
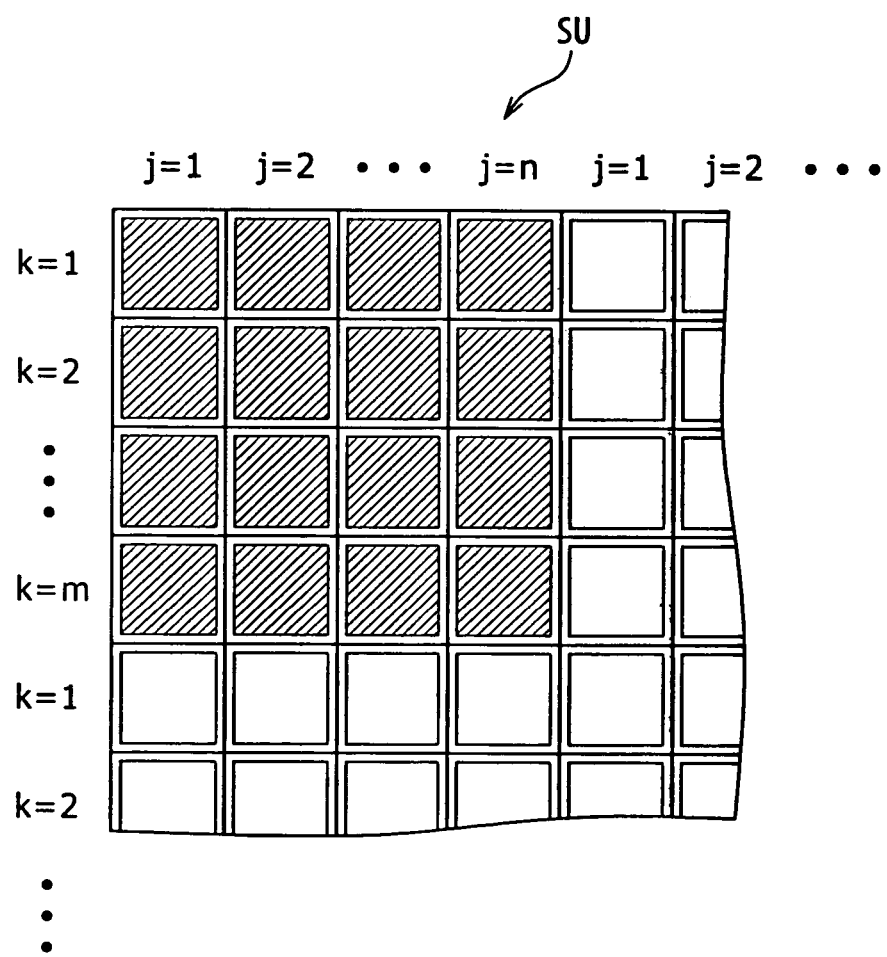
FIG. 20 is a diagrammatic view showing a detection unit of the impedance used in the blood vessel detection section of FIG. 19.

In particular, the CPU 31 controls the impedance arithmetic operation section 21 to detect the impedance of the electrodes E1 to En disposed in a grating fashion for individual unit electrode groups SUV disposed in m rows and n columns indicated by broken lines in FIG. 20.

The CPU 31 stores impedance data IP1 to IPn supplied successively thereto from the impedance arithmetic operation section 21 into the cache memory 34. Then, the CPU 31 replaces the impedance values of impedance data (hereinafter referred to as unit impedance data group) IPx (FIG. 19) corresponding to each of the unit electrode groups SU from among the impedance data IP1 to IPn stored in the cache memory 34 with a matrix of m rows and n columns.

In this state, the CPU 31 detects a minimum impedance for each of the unit electrode groups SU from the matrices. As can be recognized from the foregoing description given with reference to FIGS. 8 and 9, since the impedance decreases as the electrode disposed position approaches the blood, the position (k, j) of the minimum impedance signifies the center of a cross section of the blood vessel in the blood circulation direction.

In this manner, the CPU 31 can non-aggressively detect the presence or absence of a blood vessel (blood) based on the difference in impedance detected from each unit electrode group SU.

Figure 22:
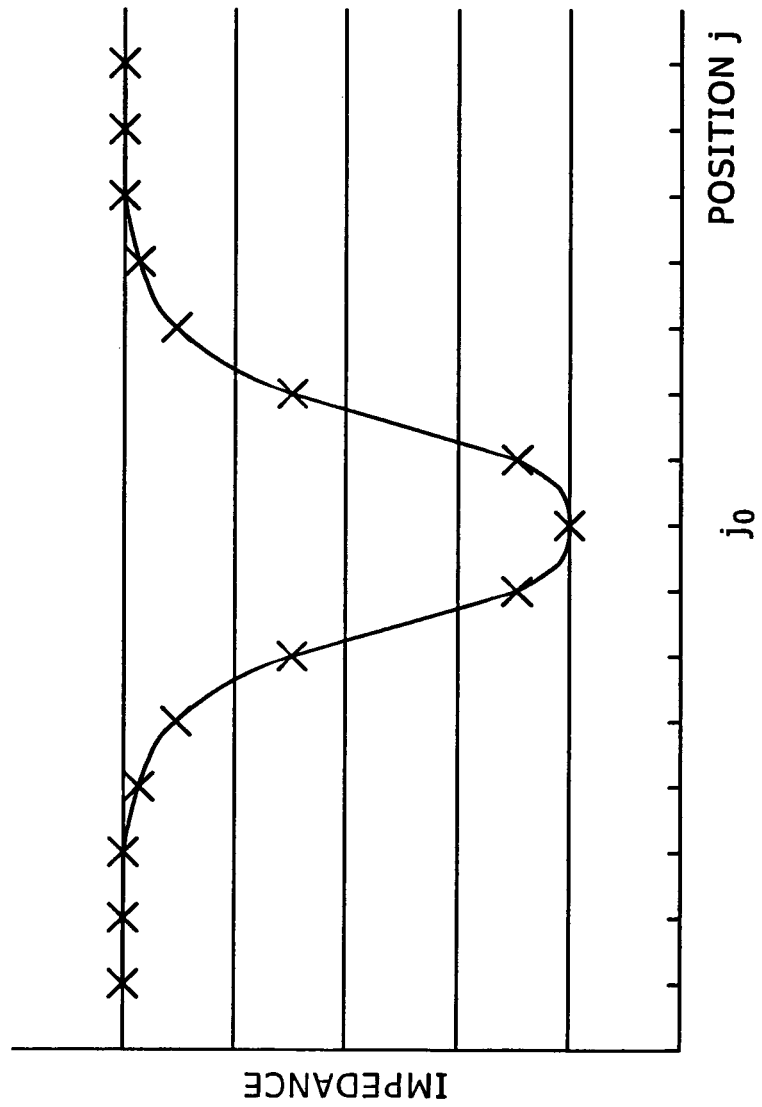
FIG. 22 is a diagram illustrating a relationship between the variation amount of the impedance around a position at which a minimum impedance is exhibited and the distance from the position.

In such a configuration as described hereinabove, when the position (k, j) of a minimum impedance is detected, the CPU 31 recognizes, for each of the unit electrode groups SU, the relationship between the degree of variation of the impedance around the position (k, j) of the minimum impedance and the distance from the position, for example, as seen from FIG. 22 and controls the EEPROM 35 so as to read out dictionary data DC recorded in advance.

Figure 23:
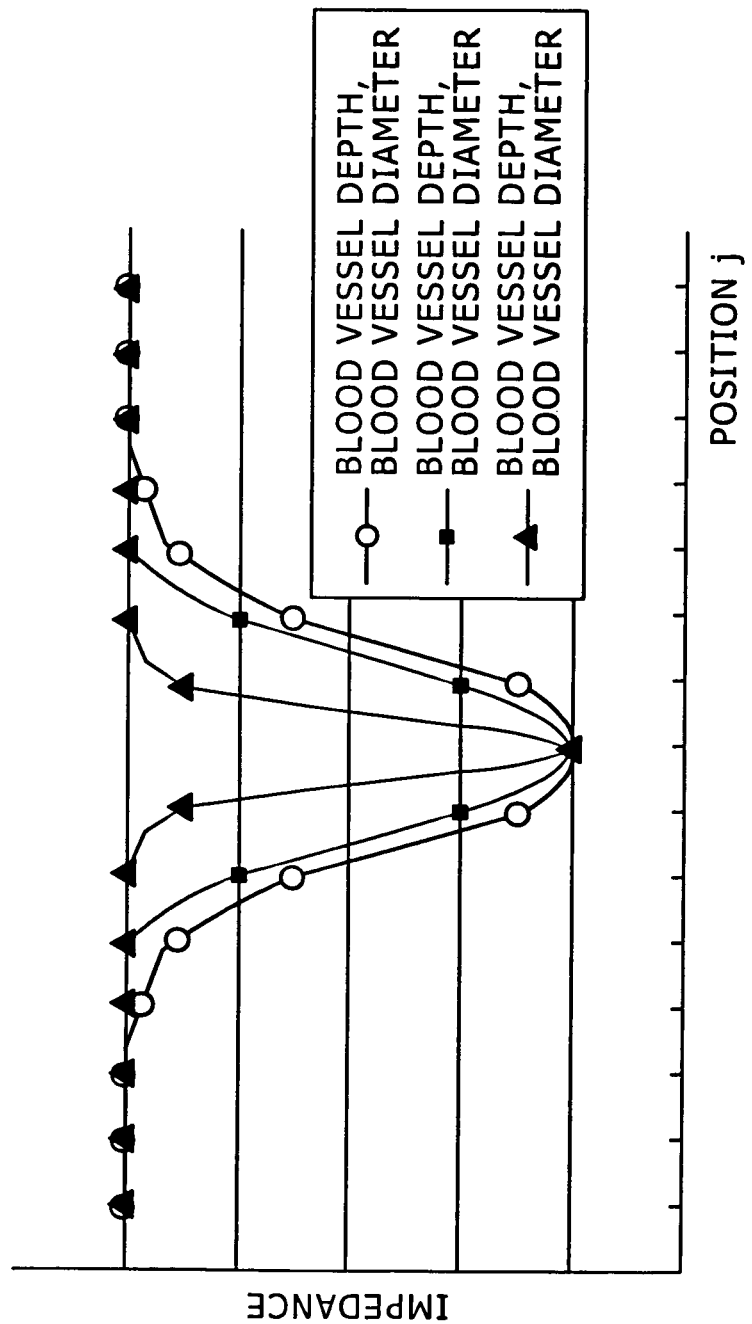
FIG. 23 is a diagram illustrating dictionary data used in the detection apparatus of FIG. 17.

The dictionary data DC coordinates the relationship of the degree of the variation of the impedance around the reference position (k, j) and the distance from the reference position with the blood vessel depth and the blood vessel diameter in the living organism as seen, for example, from FIG. 23. In FIGS. 22 and 23, the degree of the variation of the impedance around the j direction from the reference position (k, j) and the distance from the reference position are indicated for the convenience of illustration.

The CPU 31 decides the blood vessel depth and the blood vessel diameter in the living organism for each of the unit electrode groups SU based on the dictionary data DC and the relationship between the degree of variation of the impedance around the reference position (k, j) of the minimum impedance recognized then and the distance from the position.

In this manner, the CPU 31 can decide the blood vessel depth and the blood vessel diameter in response to the distance between the electrodes and the degree of variation of the impedance detected from the electrodes.

4-4. Blood Vessel Processing Procedure

Figure 24:
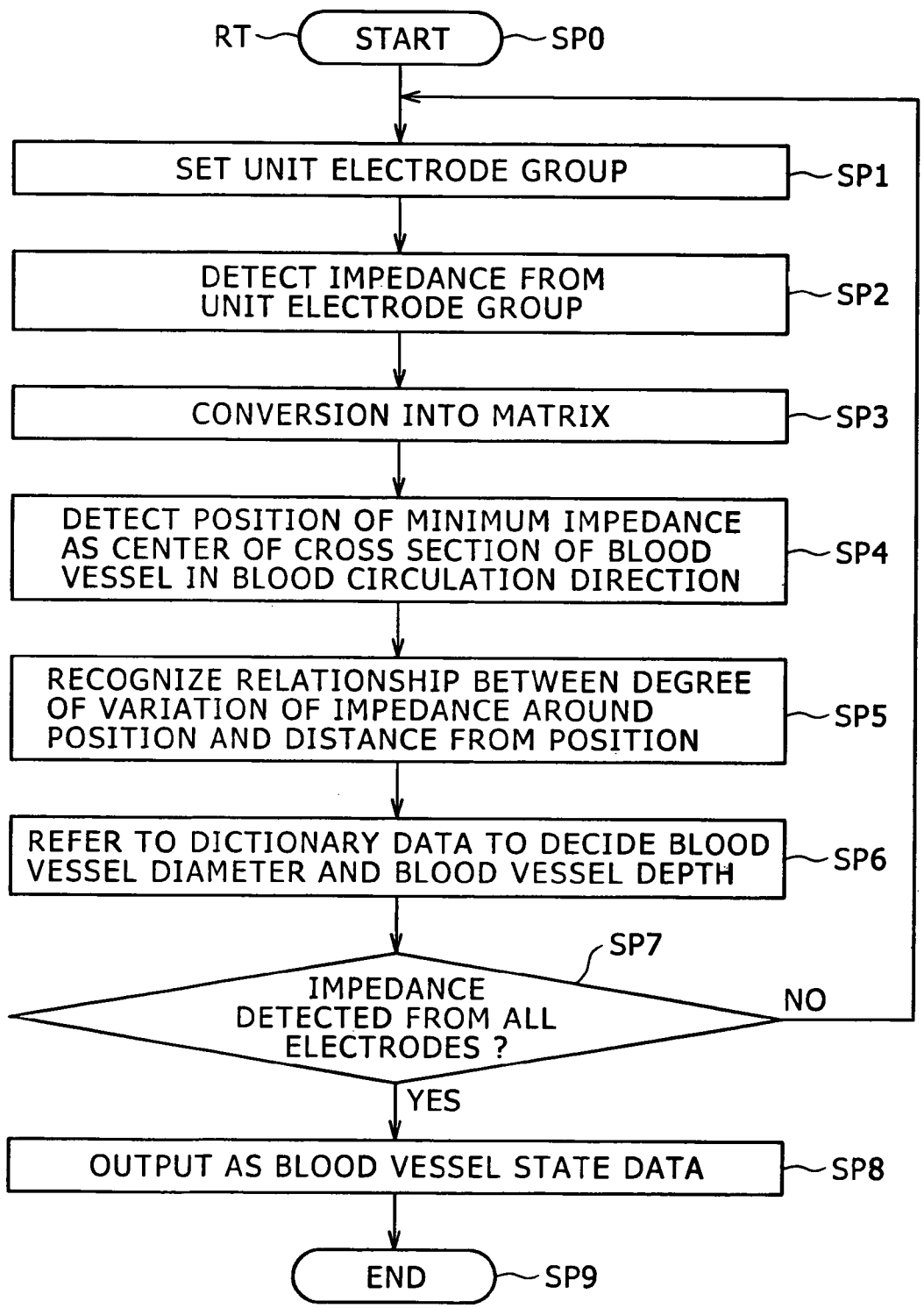
FIG. 24 is a flow chart illustrating a blood vessel detection processing procedure executed by the detection apparatus of FIG. 17.

Now, the blood vessel detection process by the CPU 31 is described with reference to a flow chart shown in FIG. 24.

In particular, for example, if a predetermined blood vessel detection starting instruction is received, then the CPU 31 starts the blood vessel detection processing procedure RT at step SP0 and then sets a unit electrode group SU (FIG. 20) of m rows and n columns, for example, at the left corner from among the electrodes E1 to En disposed in a grading fashion.

Figure 21:
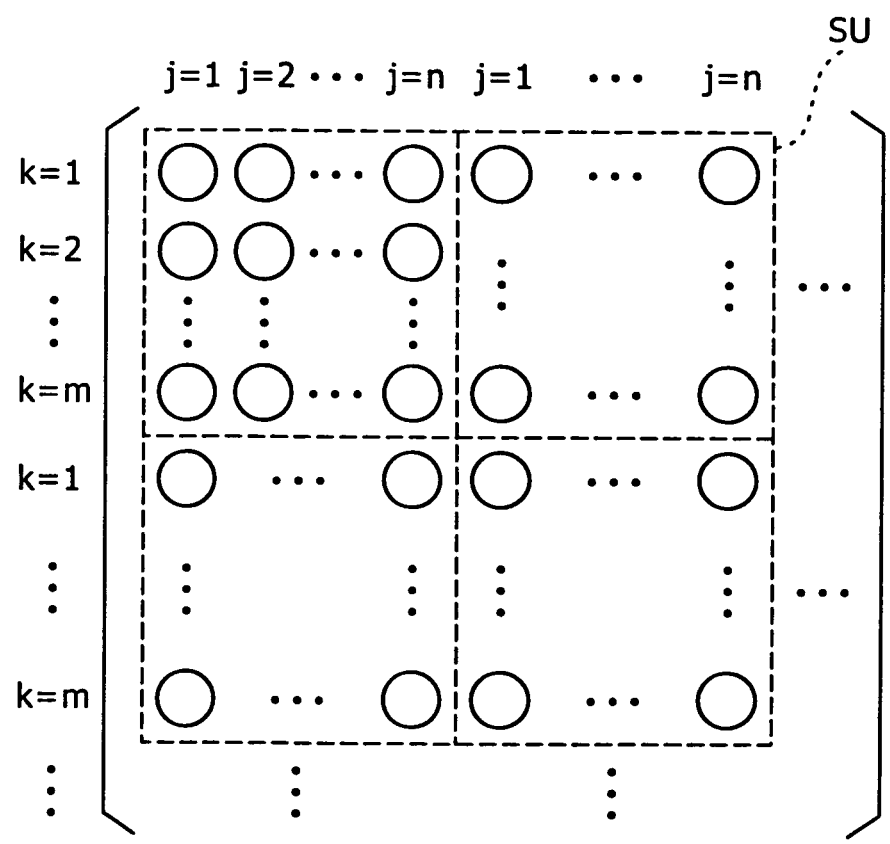
FIG. 21 is a diagrammatic view illustrating conversion into a matrix used in the blood vessel detection section of FIG. 19.

Then at step SP2, the CPU 31 detects the impedance from the unit electrode group SU set at step SP1, and replaces the detected impedance with a matrix (FIG. 21) at step SP3. Then at step SP4, the CPU 31 detects the reference position (k, j) of the minimum impedance as the center of a cross section of the blood vessel in the blood circulation direction.

At step SP5, the CPU 31 recognizes the relationship between the degree of variation of the impedance around the reference position (k, j) of the minimum impedance and the distance from the position (FIG. 2). Then at step SP6, the CPU 31 decides the blood vessel depth and the blood vessel diameter in the living organism in response to a result of the recognition and the dictionary data DC (FIG. 23). Thereafter, the processing advances to step SP7.

At step SP7, the CPU 31 decides whether or not the impedance is detected from all of the electrodes E1 to En. If a negative result is obtained, then the CPU 31 returns the processing to step SP1, at which the CPU 31 sets a unit electrode group SU to be detected subsequently. Thereafter, the processes described above are repeated.

On the other hand, if a plurality of positions are detected as positions of a minimum impedance at step SP4 when the processes described hereinabove are repeated after a unit electrode group SU to be detected is set at step SP1 to which the processing returns when the minimum impedance detected at step SP4 is higher than a predetermined threshold value and hence it is determined that no blood vessel exists, then the processes at steps SP5 and SP6 described hereinabove are executed based on the positions.

On the other hand, if an affirmative result is obtained at step SP7, then the CPU 31 outputs, at next step SP8, a matrix representative of the impedances individually detected from the electrodes E1 to En disposed in a grating-like fashion and the blood vessel depths and the blood vessel diameters detected for the individual unit electrode groups SU of the matrix as blood vessel state data. Thereafter, the processing advances to step SP9, at which the blood vessel detection processing procedure RT is ended.

In this manner, the CPU 31 can execute the blood vessel detection process.

4-5. Operation and Effects

The detection apparatus 1 having the configuration described above outputs signals in a frequency band (FIGS. 1 and 2) within which the difference in electric characteristic among various tissues of a living organism is higher than a predetermined level with a detection sensitivity and so forth taken into consideration individually to the electrodes E1 to En. In response to the outputs, quasi-electrostatic fields are generated from the electrodes E1 to En.

The detection apparatus 1 detects the impedances of the living organism disposed in the quasi-electrostatic fields individually from the electrodes E1 to En and decides presence or absence of the blood in the inside of the living organism in accordance with the differences between the detected impedances.

Accordingly, in the present detection apparatus 1, since the impedance of a quasi-electrostatic field of a frequency band in which the difference in electric characteristic between various tissues of a living organism is detected for each of the electrodes E1 to En, even if the electric characteristics of the tissues of the living organism are reflected on the impedances, whether or not the blood exists in the quasi-electrostatic fields generated from the electrodes E1 to En can be identified accurately from the electrodes E1 to En.

Further, since the frequency band in which the differences between the electric characteristics of the various tissues of the living organism are higher than a predetermined level is a low frequency region and the quasi-electrostatic fields generated in response to the signals of the low frequency band prevail in intensity over the radiation fields and the induction electromagnetic fields. Therefore, the influence of the radiation fields and the induction electromagnetic fields is not reflected on the impedances detected for the electrodes E1 to En through the quasi-electrostatic fields. Consequently, presence or absence of the blood can be identified further accurately.

Further, the detection apparatus 1 decides the width of a blood vessel (blood vessel diameter) which is provided in the inside of a living organism and contains the blood and the blood depth in the inside of the living organism with reference to the distance between the electrodes and the degree of variation of the impedance detected from the electrodes (FIGS. 11A, 11B, 12A, 12B, 22 and 23).

Accordingly, the detection apparatus 1 can acquire a great amount of information relating to the blood accurately and non-aggressively.

With the detection apparatus 1 having the configuration described above, signals in a frequency band in which the differences between electric characteristics of various tissues of a living organism are higher than a predetermined level are outputted individually to the electrodes E1 to En, and the impedances of the living organism disposed in quasi-electrostatic fields generated from the electrodes E1 to En in response to the outputs are detected. Then, the presence or absence of the blood in the inside of the living organism is detected in response to the differences between the impedances. Consequently, whether or not the blood exists in the quasi-electrostatic fields generated from the electrodes E1 to En can be identified accurately from the electrodes E1 to En, and therefore, the blood can be detected with a high degree of accuracy.

5. Second Embodiment 5-1. Configuration of the Authentication Apparatus

Figure 25:
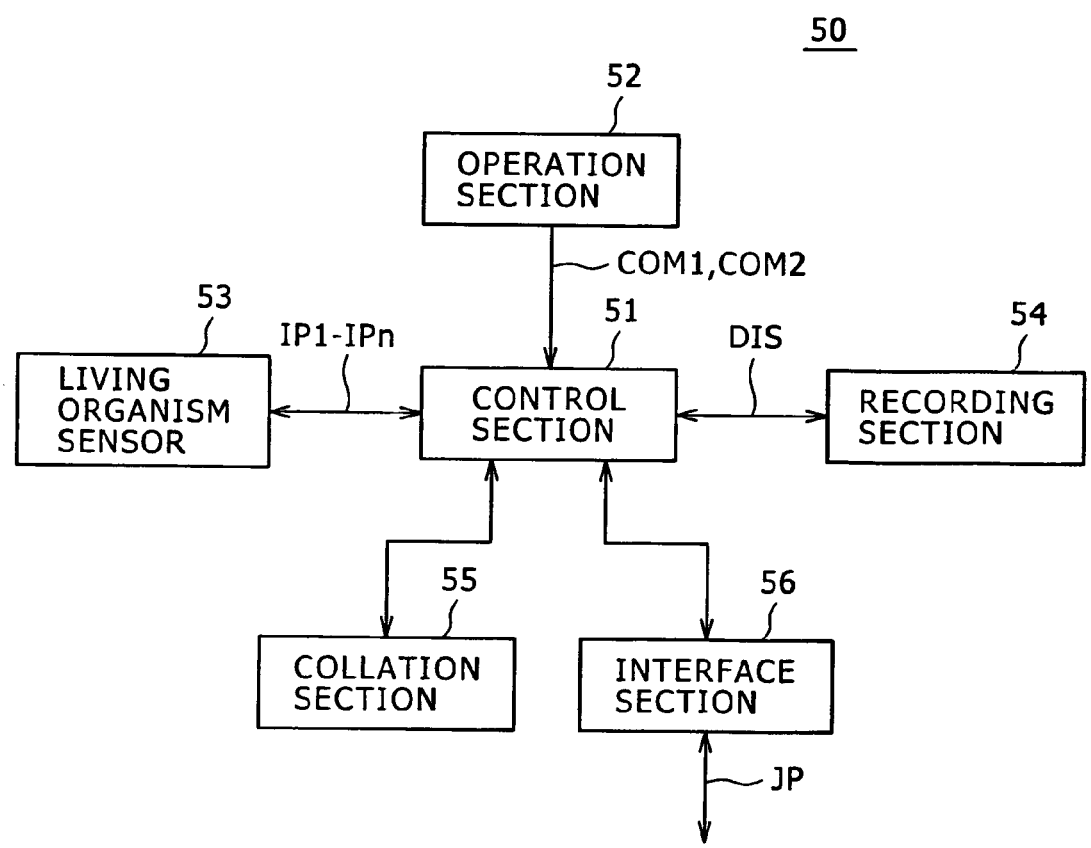
FIG. 25 is a block diagram showing a configuration of an authentication apparatus to which the second embodiment of the present invention is applied.

An authentication apparatus in which the blood vessel detection function in the first embodiment is incorporated is shown in FIG. 25. Referring to FIG. 25, the authentication apparatus 50 includes an operation section 52, a living organism sensor 53, a recording section 54, a collation section 55, and an interface section 56 all connected to a control section 51 individually by buses. The interface section 56 transmits and receives data to and from the outside of the authentication apparatus 50.

The living organism sensor 53 has a configuration same as that of the impedance detection section 2 described hereinabove with reference to FIG. 17. Meanwhile, the recording section 54 may be, for example, an optical disk drive into which an optical disk can be removably loaded.

The control section 51 has a computer configuration including a CPU for controlling the entire authentication apparatus 50, a ROM in which various programs and setting information are stored, a RAM serving as a working memory for the CPU, and a cache memory. To the control section 51, an execution command COM1 of a mode for registering a blood vessel of a registered person (the mode is hereinafter referred to as blood registration mode) and an execution command COM2 of another mode for deciding presence or absence of the registered person itself (the mode is hereinafter referred to as authentication mode) are provided from the operation section 52 in response to a user operation.

The control section 51 determines a mode to be executed based on the execution command COM1 or COM2 and suitably controls the living organism sensor 53, recording section 54, collation section 55, and interface section 56 in accordance with a program corresponding to a result of the determination to execute a registration process or an authentication process.

More particularly, if the blood registration mode is determined as a mode to be executed, then the control section 51 sets the operation mode to the blood registration mode and controls the living organism sensor 53 to execute the processes at steps SP1 to SP7 of the blood vessel detection processing procedure RT described hereinabove with reference to FIG. 24. In the process, the impedances detected through the electrodes E1 to En disposed in a grating-like fashion are replaced with matrices (FIG. 21), and a blood vessel diameter and a blood vessel depth are obtained for each of the unit electrode groups SU of the matrices.

The control section 51 detects branching points of blood vessels and the depth of the branching points based on the matrices (FIG. 21) and the blood vessel diameters and blood vessel depths and produces the detected blood vessel branching points and depths of the branching points as personal identification data DIS. Then, the control section 51 controls the recording section 54 to record the personal identification data DIS. The personal identification data DIS is registered on a recording medium by the recording section 54 under the control of the control section 51.

In this manner, the control section 51 can execute the blood registration mode.

On the other hand, if the authentication mode is determined as the mode to be executed, then the control section 51 enters the authentication mode and detects blood vessel branching points and the depths of the blood vessel branching points based on the impedance data IP1 to IPn acquired from the living organism sensor 53 in a similar manner as in the case of the blood vessel registration mode described above. Then, the control section 51 controls the collation section 55 to collate the detected blood vessel branching points and depths with the personal identification data DIS.

The collation section 55 acquires the personal identification data DIS from the recording section 54 and collates the blood vessel branching points and the depths of the branching points of the personal identification data DIS with the blood vessel branching points and the depths of the branching points of a corresponding comparison object, respectively, under the control of the control section 51.

Further, the collation section 55 decides in response to the degree of the collation whether or not the user who currently is a detection object of the living organism sensor 53 is a registered person (legal user). Then, the collation section 55 transfers a result of the decision as decision data JD to the outside through the interface section 56.

In this manner, the control section 51 can execute the authentication mode.

5-2. Operation and Effects

The authentication apparatus 50 having the configuration described above detects the width of each of the blood vessels (blood vessel diameter) which contain the blood in the inside of a living organism and the blood vessel depth in the inside of the living organism with reference to the distance between the electrodes and the degree of variation of the impedance detected from the electrodes. Then, the authentication apparatus 50 produces blood vessel branching points and the depths of the blood vessel branching points as personal identification data DIS based on the detected widths of the blood vessels (blood vessel diameters) and blood vessel depths in the inside of the living organism.

Accordingly, since identification parameters in the inside of the living organism are produced not only as planar position information but also as three-dimensional information, the authentication apparatus 50 can identify an individual person accurately and can prevent impersonation of a third party.

In the authentication apparatus 50 having the configuration described above, blood vessel branching points and the depths of the blood vessel branching points are produced as personal identification data DIS based on widths of the blood vessels (blood vessel diameters), which contain the blood, and blood vessel depths in the inside of the living organism. Therefore, identification parameters in the inside of the living organism can be produced not only as planar position information but also as three-dimensional information, and consequently, an individual person can be identified accurately and impersonation of a third party can be prevented.

6. Third Embodiment 6-1. Information Providing Apparatus

Figure 26:
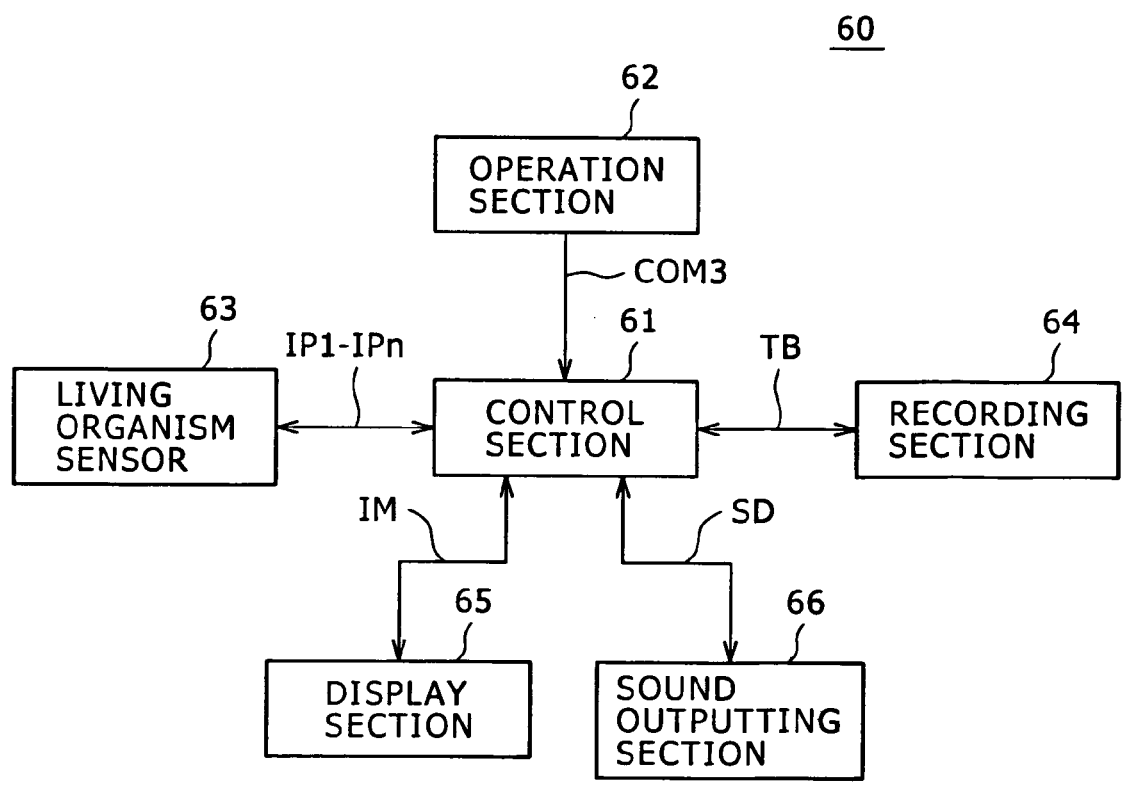
FIG. 26 is a block diagram showing a configuration of an information providing apparatus to which the third embodiment of the present invention is applied.

An information processing apparatus which incorporates the blood vessel detection function in the first embodiment is shown in FIG. 26. Referring to FIG. 26, the information providing apparatus 60 shown includes an operation section 62, a living organism sensor 63, a recording section 64, a display section 65, and a sound outputting section 66 connected to a control section 61 by individual buses.

The living organism sensor 63 has a configuration same as that of the impedance detection section 2 described hereinabove with reference to FIG. 17. The recording section 64 may be, for example, an optical disk drive into which an optical disk can be removably loaded.

The control section 61 has a computer configuration including a CPU for controlling the entire information providing apparatus 60, a ROM in which various programs and setting information are stored, a RAM serving as a working memory for the CPU, and a cache memory. To the control section 61, an execution command COM3 for detecting a blood vessel state is provided from the operation section 62 in response to a user operation.

The control section 61 suitably controls the living organism sensor 63, recording section 64, display section 65, and sound outputting section 66 in accordance with a program corresponding to the execution command COM3 to execute a blood vessel state notification process.

More particularly, the control section 61 controls the living organism sensor 63 to execute the processes at steps SP1 to SP4 and SP7 of the blood vessel detection processing procedure RT described hereinabove with reference to FIG. 24. In the process, the impedances detected through the electrodes E1 to En disposed in a grating-like fashion are replaced with matrices (FIG. 21), and the reference position (k, j) of a minimum impedance is obtained for each of the unit electrode groups SU of the matrices.

The control section 61 detects the specific dielectric constant of a blood vessel from an average value of the minimum impedances in each of the unit electrode groups SU and thereafter controls the recording section 64 so as to read out a table TB recorded in advance. In the table TB, the range of the viscosity is divided into a normal range and other deviation ranges including a slight deviation range, a medium deviation range, and a serious deviation range determined based on the degree of deviation from the normal range. The table TB thus coordinates different blood vessel viscosities with the ranges.

The control section 61 refers to the table TB to detect to which range each determined specific dielectric constant corresponds and controls the recording section 64 to record the specific dielectric constant and the blood viscosity range corresponding to the specific dielectric constant as a history on the recording medium.

The control section 61 produces image data IM and sound data SD to be used for notification of the blood viscosity based on the specific dielectric constants and blood viscosity ranges as well as specific dielectric constants and blood viscosity ranges recorded in the past. Then, the control section 61 controls the display section 65 so as to display a display screen based on the image data IM and controls the sound outputting section 66 so as to output sound based on the sound data SD.

The display section 65 displays, for example, a graph whose axis of ordinate indicates the blood viscosity and whose axis of abscissa indicates the date and hour at a central portion of the screen under the control of the control section 61. Further, the display section 65 plots the normal range of the blood viscosity and the blood viscosity trend of the user in the graph and displays a comment corresponding to the blood viscosity range like "your blood is not viscous" under the control of the control section 61.

Meanwhile, the sound outputting section 66 outputs a voice comment corresponding to the blood viscosity range like, for example, "Your blood currently is not viscous." under the control of the control section 61.

In this manner, the control section 61 causes the blood viscosity trend of the user to be displayed as a graph together with the normal range and causes the state of the blood viscosity of the user with respect to the normal range to be displayed as a comment. Consequently, it is possible to allow the user to intuitively grasp an item relating to the blood viscosity of the user itself at a glance.

In this manner, the control section 61 can issue a notification of the blood viscosity as an index to the condition of the health.

6-2. Operation and Effects

The information providing apparatus 60 having the configuration described above outputs signals in a frequency band (FIGS. 1 and 2) in which the differences between electric characteristics of various tissues of a living organism are higher than a predetermined level to the plural electrodes E1 to En and decides presence or absence of the blood in the inside of the living organism in response to the differences between the impedances of the living organism disposed in quasi-electrostatic fields generated from the electrodes E1 to En in response to the outputs.

Then, the information providing apparatus 60 decides the ratio between the blood cells and the blood serum of the blood in response to the impedance values detected from those of the electrodes E1 to En on the side on which the blood exists in the quasi-electrostatic fields generated from the electrodes.

Accordingly, even if electric characteristics of various tissues of a living organism are reflected on the impedances, the information providing apparatus 60 can identify presence or absence of the blood accurately as described hereinabove in the paragraph 4-5, which describes the operation and effects of the first embodiment. Therefore, also the ratio between the blood cells and the blood serum of the blood (blood viscosity) can be decided accurately in response to the impedance values.

With the information providing apparatus 60 having the configuration described above, the ratio between the blood cells and the blood serum of the blood is decided in response to the impedance values detected from those of the electrodes E1 to En on the side on which the blood exists in quasi-electrostatic fields generated from the electrodes. Consequently, even if electric characteristics of various tissues of a living organism are reflected on the impedances, the ratio between the blood cells and the blood serum of the blood (blood viscosity) can be decided accurately. Consequently, the information relating to the inside of the living organism can be provided with a high degree of accuracy.

7. Other Embodiments

It is to be noted that, while, in the embodiments described above, signals having a fixed amplitude and a frequency of 1 MHz are outputted, according to the present invention, the signals to be outputted are not limited to them. In particular, various signals can be outputted only if the signals are within a frequency band within which the differences of electric characteristics of various tissues of a living organism have a level higher than a predetermined level. In this instance, as described hereinabove, it should be used as an index in what low frequency band the conductivity and the specific dielectric constant of tissues of a living organism of an object of detection can be identified clearly from those of the other tissues or at what depth a tissue of a living organism of an object of detection exists from the surface of the organism.

Further, while, in the embodiments described above, electrodes for exclusive use are used, alternatively a substrate provided in the detection apparatus 1, authentication apparatus 50, or information providing apparatus 60 may be applied for the electrodes.

Further, while, in the embodiments described above, the impedance detection section 2 shown in FIG. 17 is applied, according to an embodiment of the present invention, detection of the impedance is not limited to this. In particular, impedance detection sections of various configurations can be applied only if impedances of a living organism disposed in quasi-electrostatic fields generated from the individual electrodes are detected individually from the electrodes.

For example, an impedance detection section may be applied which includes amplifiers interposed between the electrodes E1 to En and the corresponding ammeters CM1 to CMn. Since the impedance detection section can accurately detect a potential variation of quasi-electrostatic fields detected from the electrodes E1 to En, the variation in impedance of a living organism tissue can be detected with a higher degree of accuracy.

Figure 27:
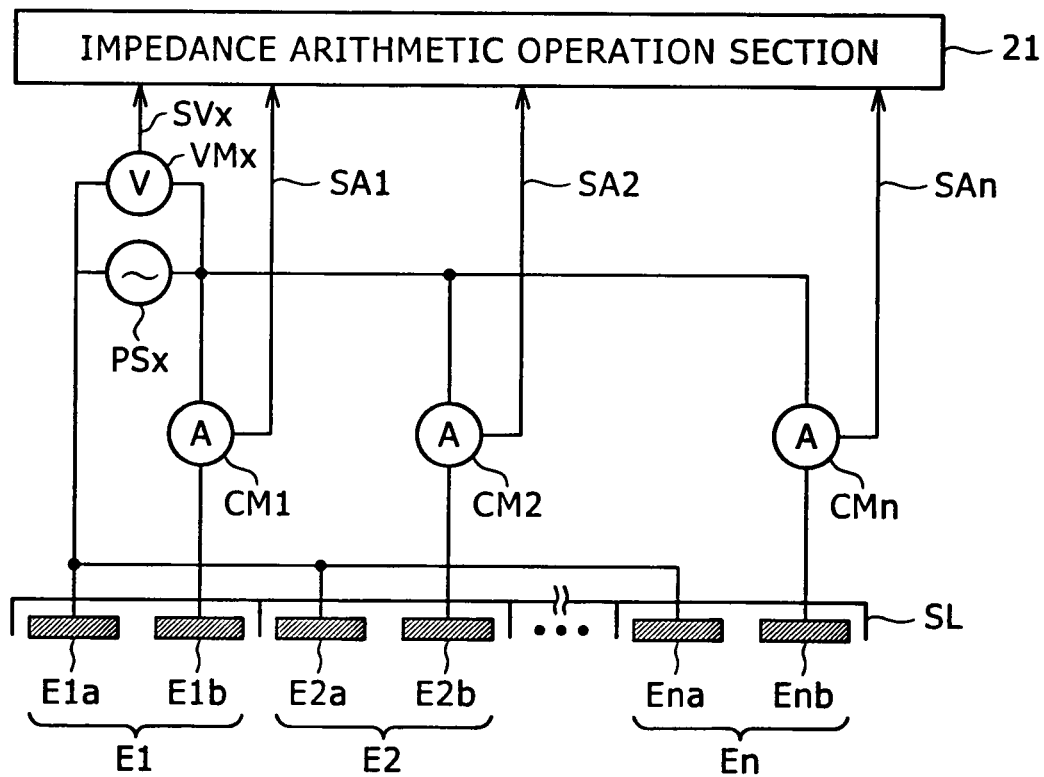
FIG. 27 is a schematic view showing a configuration of a modified impedance detection section which can be incorporated in the detection apparatus of FIG. 17.

Further, for example, while the impedance detection section 2 shown in FIG. 17 includes the signal supplying sources PS1 to PSn and the voltmeters VM1 to VMx individually corresponding to the electrodes E1 (E1$a$, E1$b$) to En (En$a$, En$b$), the signal supplying sources PS1 to PSn and the voltmeters VM1 to VMx may be replaced by a common signal supplying source and voltmeter (signal supplying source PSx and voltmeter VMx) as seen in FIG. 27.

In this instance, similar effects to those of the embodiments described hereinabove can be achieved if the impedance arithmetic operation section 21 determines impedance values corresponding to the electrodes E1 to En from the ratio between the measurement result SA1 by the ammeter CM1 and the measurement result SVx by the voltmeter VMx, the ratio between the measurement result SA2 by the ammeter CM2 and the measurement result SVx by the voltmeter VMx, . . . , and the ratio between the measurement result SAn by the ammeter CMn and the measurement result SVx by the voltmeter VMx, respectively.

Further, while, in the embodiments described above, presence or absence of the blood is detected, an embodiment of the present invention is not limited to the blood. For example, an embodiment of the present invention can be applied to detection of sol such as bone marrow fluid, cerebrospinal fluid, or lymphatic fluid, flatus or intrapulmonary gas, and other various colloids in the inside of a living organism. In this instance, if the disposed position of the electrodes and/or the frequency of signals to be applied to the electrodes are suitably changed in response to the type of the colloid, then presence or absence of the object colloid can be detected similarly as in the embodiments described above.

Further, while, in the embodiments described hereinabove, the width of a blood vessel (blood vessel diameter), which contains the blood, and the depth of the blood (blood vessel) in the inside of a living organism are decided, an embodiment of the present invention is not limited to them. An embodiment of the present invention can be applied to decision of tomographic images of various other tissues. For example, an embodiment of the present invention can be applied to decision of the width and the depth of a bone marrow tissue which contains bone marrow fluid, the width and the depth of a cerebrospinal tissue which contains cerebrospinal fluid, the width and the depth of a lymph vessel which contains lymphatic fluid, the width and the depth of a large intestine tissue, which contains flatus, and the width and the depth of a lung tissue which contains intrapulmonary gas.

Further, while, in the embodiments described hereinabove, the blood viscosity is decided based on an electric characteristic of the blood, an embodiment of the present invention is not limited to this. For example, according to an embodiment of the present invention, a state of a tissue may be decided based on an electric characteristic of bone marrow fluid, cerebrospinal fluid, lymphatic fluid, flatus, or intrapulmonary gas.

Furthermore, while, in the embodiments described hereinabove, only the blood viscosity (state of blood) is decided, additionally a predetermined disease may be estimated in response to a result of the decision.

For such decision, particularly bone marrow fluid, cerebrospinal fluid, or lymphatic fluid can be applied effectively to the estimation. Although leukemia of a bone marrow system or a lymphatic system has been decided from the shape of a blood cell, flow cytometry is available instead in recent years. According to the flow cytometry, fluorescence-labeled monoclonal antibody is coupled to cells in bone marrow fluid taken as a sample from a patient, and leukemia is decided based on scattered light when laser light is irradiated upon the cells. In this manner, in the flow cytometry, leukemia is decided using the surface structure of a cell as an index.

In contrast, if leukemia is estimated (decided) based on an electric characteristic of bone marrow fluid, cerebrospinal fluid, or lymphatic fluid, then since a feature which arises not from the surface structure of a cell but from a variation of a cell itself is taken as a variation of the impedance, it can be used as one of new indices. Therefore, further enhance of the accuracy in decision of leukemia can be anticipated. Further, since the decision can be made non-aggressively, no burden is imposed on the patient. Consequently, the cure effect and so forth can be observed usefully on the real-time basis.

Furthermore, while, in the embodiments described hereinabove, a tomographic image of a blood vessel (blood vessel diameter and blood vessel depth) is decided, an embodiment of the present invention is not limited to this. In particular, according to an embodiment of the present invention, a time axis region may be additionally taken into consideration to decide also the pulsation in the blood vessel.

An embodiment of the present invention can be applied to identification of a living organism or decision of a state of a living organism.

It should be understood by those skilled in the art that various modifications, combinations, sub-combinations and alternations may occur depending on design requirements and other factors insofar as they are within the scope of the appended claims or the equivalent thereof.

What is claimed is:

1. A detection apparatus, comprising:
signal outputting means configured to output signals of a frequency band to electrodes;
impedance detection means configured to detect, through the electrodes, impedances of a living organism in response to the signals, wherein the living organism is disposed in quasi-electrostatic fields generated by the electrodes in response to the signals;
detection means configured to detect the presence or absence of a blood vessel in the living organism by detecting minimum impedances for unit electrode groups, wherein each unit electrode group includes more than one electrode; and
state decision means configured to detect a diameter of the blood vessel in the living organism for at least one unit electrode group by comparing:
pre-recorded dictionary data coordinating relationships between a degree of variation of an impedance around a reference position and a distance from the reference position for blood vessels having certain diameters, and
a measured relationship between a degree of variation of the impedances around a position of the minimum impedance detected by the electrodes in the at least one unit electrode group and a distance from the position,
wherein the frequency band is selected such that a difference in electric characteristics between different tissues of the living organism detected using the signals is higher than a predetermined level.

2. The detection apparatus of claim 1, further comprising production means configured to produce a shape and a depth of the blood vessel as identification signals for identifying the living organism.

3. The detection apparatus of claim 2, further comprising identification means configured to identify the living organism based on the shape and the depth of the blood vessel.

4. The detection apparatus of claim 1, further comprising blood viscosity decision means configured to decide the blood viscosity of the blood vessel in response to the impedances.

5. A detection method, comprising:
outputting signals of a frequency band to electrodes;
detecting, through the electrodes, impedances of a living organism in response to the signals, wherein the living organism is disposed in quasi-electrostatic fields generated by the electrodes in response to the signals;
detecting the presence or absence of a blood vessel in the living organism by detecting a minimum impedance for unit electrode groups, wherein each unit electrode group includes more than one electrode; and
detecting a diameter of the blood vessel in the living organism for at least one unit electrode group by comparing:
pre-recorded dictionary data coordinating relationships between a degree of variation of an impedance around a reference position and a distance from the reference position for blood vessels having certain diameters, and
a measured relationship between a degree of variation of the impedances around a position of the minimum impedance detected by the electrodes in the at least one unit electrode group and a distance from the position,
wherein the frequency band is selected such that a difference in electric characteristics between different tissues of the living organism detected using the signals is higher than a predetermined level.

6. A detection apparatus, comprising:
a signal outputting section for outputting signals of a frequency band to electrodes;
an impedance detection section for detecting, through the electrodes, impedances of a living organism in response to the signals, wherein the living organism is disposed in quasi-electrostatic fields generated by the electrodes in response to the signals;
a detection section for detecting the presence or absence of a blood vessel in the living organism by detecting a minimum impedance for unit electrode groups, wherein each unit electrode group includes more than one electrode; and
a state decision section for detecting a diameter of the blood vessel in the living organism for at least one unit electrode group by comparing:
pre-recorded dictionary data coordinating relationships between a degree of variation of an impedance around a reference position and a distance from the reference position for blood vessels having certain diameters, and
a measured relationship between a degree of variation of the impedances around a position of the minimum impedance detected by the electrodes in the at least one unit electrode group and a distance from the position,
wherein the frequency band is selected such that a difference in electric characteristics between different tissues of the living organism detected using the signals is higher than a predetermined level.

* * * * *

UNITED STATES PATENT AND TRADEMARK OFFICE
CERTIFICATE OF CORRECTION

| | | |
|---|---|---|
| PATENT NO. | : 8,634,905 B2 | Page 1 of 1 |
| APPLICATION NO. | : 11/636572 | |
| DATED | : January 21, 2014 | |
| INVENTOR(S) | : Takiguchi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 377 days.

Signed and Sealed this
Twenty-first Day of July, 2015

Michelle K. Lee
*Director of the United States Patent and Trademark Office*